US012076328B2

(12) United States Patent
Williams, III et al.

(10) Patent No.: US 12,076,328 B2
(45) Date of Patent: Sep. 3, 2024

(54) PHARMACEUTICAL COMPOSITIONS OF NICLOSAMIDE

(71) Applicant: BOARD OF REGENTS, THE UNIVERSITY OF TEXAS SYSTEM, Austin, TX (US)

(72) Inventors: Robert O. Williams, III, Austin, TX (US); Hugh D. C. Smyth, Austin, TX (US); Zachary N. Warnken, Austin, TX (US); Miguel Orlando Jara Gonzalez, Austin, TX (US); Hyo-Jong Seo, Austin, TX (US); Ashlee D. Brunaugh, Austin, TX (US); Matthew Herpin, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 227 days.

(21) Appl. No.: 17/220,833

(22) Filed: Apr. 1, 2021

(65) Prior Publication Data
US 2021/0322445 A1    Oct. 21, 2021

Related U.S. Application Data

(60) Provisional application No. 63/003,793, filed on Apr. 1, 2020.

(51) Int. Cl.
| | |
|---|---|
| *A61K 31/609* | (2006.01) |
| *A61K 9/00* | (2006.01) |
| *A61K 47/10* | (2017.01) |
| *A61K 47/32* | (2006.01) |
| *A61K 47/58* | (2017.01) |

(52) U.S. Cl.
CPC .......... *A61K 31/609* (2013.01); *A61K 9/0053* (2013.01); *A61K 47/10* (2013.01); *A61K 47/32* (2013.01); *A61K 47/58* (2017.08)

(58) Field of Classification Search
CPC ...... A61K 31/609; A61K 47/10; A61K 47/32; A61K 47/58
See application file for complete search history.

(56) References Cited

U.S. PATENT DOCUMENTS

| | | | |
|---|---|---|---|
| 7,544,712 B1 | 6/2009 | Hsu et al. | |
| 8,486,423 B2 | 7/2013 | Brough et al. | |
| 8,968,786 B2 | 5/2015 | Johnston et al. | |
| 9,089,589 B2 * | 7/2015 | Mohapatra | C12Q 1/6809 |
| 9,339,440 B2 | 5/2016 | Brough et al. | |
| 2010/0221343 A1 | 9/2010 | Johnston et al. | |
| 2016/0193151 A1 * | 7/2016 | Noriega Escobar | A61K 31/554 562/460 |
| 2019/0343783 A1 | 11/2019 | Yook et al. | |

FOREIGN PATENT DOCUMENTS

| | | |
|---|---|---|
| CN | 110 833 623 | 2/2020 |
| WO | WO 2009/108077 | 9/2009 |
| WO | WO 2017/223491 | 12/2017 |
| WO | WO 2021/202928 | 10/2021 |

OTHER PUBLICATIONS

Barbosa et al., "Niclosamide repositioning for treating cancer: Challenges and nano-based drug delivery opportunities", *Eur. J. Pharm. Biopharm.*, 141:58-69, 2019.
Beinborn et al., "Dry powder insufflation of crystalline and amorphous voriconazole formulations produced by thin film freezing to mice", *European journal of pharmaceutics and biopharmaceutics*, 81(3):600-8, 2012a.
Beinborn et al., "Effect of process variables on morphology and aerodynamic properties of voriconazole formulations produced by thin film freezing", *Int J Pharmaceutics.*, 429(1-2):46-57, 2012b.
Bray et al., "Global cancer statistics 2018: GLOBOCAN estimates of incidence and mortality worldwide for 36 cancers in 185 countries", *CA: A Cancer Journal for Clinicians*, 68(6):394-424, 2018.
Carvalho et al., "Characterization and pharmacokinetic analysis of crystalline versus amorphous rapamycin dry powder via pulmonary administration in rats", *European journal of pharmaceutics and biopharmaceutics*, 88(1):136-47, 2014.
Chen et al., "Niclosamide: Beyond an antihelminthic drug", *Cell. Signal.*, 41:89-96, 2018.
Circu et al., "A Novel High Content Imaging-Based Screen Identifies the Anti-Helminthic Niclosamide as an Inhibitor of Lysosome Anterograde Trafficking and Prostate Cancer Cell Invasion", *PLOS One*, 11:e0146931, 2016.
Costabile et al, Toward Repositioning Niclosamide for Antivirulence Therapy of Pseudomonas aeruginosa Lung infections: Development of Inhalable Formulations through Nanosuspension Technology, Molecular Pharmaceutics, 12:2604-2617, 2015.
Crowley et al., "Pharmaceutical Applications of Hot-Melt Extrusion: Part I", *Drug Dev. Ind. Pharm.*, 33(10):909-926, 2007.
Devarakonda et al., "Comparison of the aqueous solubilization of practically insoluble niclosamide by polyamidoamine (PAHAM) dendrimers and cyclodextrins", *International Journal of Pharmaceutics*, 304(1-2):193-209, (2005).
DiNunzio et al., "Amorphous compositions using concentration enhancing polymers for improved bioavailability of itraconazole", *Mol Pharm.*, 5(6):968-80, 2008.
DiNunzio et al., "Applications of KinetiSol® Dispersing for the production of plasticizer free amorphous solid dispersions", *European Journal of Pharmaceutical Sciences*, 40(3):179-87, 2010c.
DiNunzio et al., "Fusion processing of itraconazole solid dispersions by kinetisol dispersing: a comparative study to hot melt extrusion", *Journal of Pharmaceutical Sciences*, 99(3):1239-53, 2010b.

(Continued)

*Primary Examiner* — Sahar Javanmard
(74) *Attorney, Agent, or Firm* — Parker Highlander PLLC

(57) ABSTRACT

The present disclosure provides pharmaceutical compositions of niclosamide that may be administered either orally or by inhalation. These compositions may allow the achievement of a therapeutically effective dose of niclosamide to the lungs or the gastrointestinal tract. These compositions may be used to treat one or more diseases or disorders such as a viral infection or cancer.

14 Claims, 15 Drawing Sheets

(56) References Cited

OTHER PUBLICATIONS

DiNunzio et al., "Fusion production of solid dispersions containing a heat-sensitive active ingredient by hot melt extrusion and Kinetisol dispersing", *European Journal of Pharmaceutics and Biopharmaceutics*, 74(2):340-51, 2010a.

DiNunzio et al., "Production of advanced solid dispersions for enhanced bioavailability of itraconazole using KinetiSol Dispersing", *Drug Development and Industrial Pharmacy*, 36(9):1064-78, 2010d.

Dubey et al., "Fabrication of electrospun poly(ethylene oxide)-poly(caprolactone) composite nanofibers for co-delivery of niclosamide and silver nanoparticles exhibits enhanced anti-cancer effects in vitro", *Journals of Materials Chemistry B*, 4:726-742, 2016.

Engstrom et al., "Formation of stable submicron protein particles by thin film freezing", Pharm Res.; 25(6):1334-46, 2008.

Fang et al., "Are patients with hypertension and diabetes mellitus at increased risk for COVID-19 infection? ", *Lancet Respir. Med.*, 2020.

Fonseca et al., "Structure-activity analysis of niclosamide reveals potential role for cytoplasmic pH in control of mammalian target of rapamycin complex 1 (mTORC1) signaling", *J. Biol. Chem.*, 287:17530-17545, 2012.

Friesen et al., "Hydroxypropyl methylcellulose acetate succinate-based spray-dried dispersions: an overview", *Molecular pharmaceutics*, 5(6):1003-19, 2008.

Gassen et al., "SKP2 attenuates autophagy through Beclin1-ubiquitination and its inhibition reduces MERS—Coronavirus infection", *Nat. Commun.*, 10:1-16, 2019.

Hoffmann et al., "SARS-COV-2 Cell Entry Depends on ACE2 and TMPRSS2 and is Blocked by a Clinically Proven Protease Inhibitor", *Cell*, 181(2):271-280,2020.

Hughey et al., "Dissolution Enhancement of a Drug Exhibiting Thermal and Acidic Decomposition Characteristics by Fusion Processing: A Comparative Study of Hot Melt Extrusion and KinetiSol® Dispersing", *AAPS PharmSciTech*, 11(2), 2010.

Hughey et al., "Thermal processing of a poorly water-soluble drug substance exhibiting a high melting point: The utility of KinetiSol® Dispersing", *International Journal of Pharmaceutics*, 419(1):222-30, 2011.

Ippolito et al., "Extracellular pH Modulates Neuroendocrine Prostate Cancer Cell Metabolism and Susceptibility to the Mitochondrial Inhibitor Niclosamide", *PloS One*, 11(7):e0159675, 2016.

Jeon et al., "Identification of Antiviral Drug Candidates against SARS-COV-2 from FDA-Approved Drugs", Antimicrob Agents Chemother 64(7) 19-20,2020.

Jurgeit et al., "Niclosamide is a proton carrier and targets acidic endosomes with broad antiviral effects", *PloS Pathog.*, 8(10), 2012.

Keen et al., "Enhancing bioavailability through thermal processing", *Int. J. Pharm.*, 450(1-2):185-196, 2013.

Kim and Ryan, "Androgen receptor directed therapies in castration-resistant metastatic prostate cancer", *Current Treatment Options in Oncology*, 13(2):189-200, 2012.

LaFountaine et al., "Challenges and Strategies in Thermal Processing of Amorphous Solid Dispersions: A Review", *AAPS PharmSciTech*, 17(1):43-55, 2016a.

LaFountaine et al., "Enabling thermal processing of ritonavir-polyvinyl alcohol amorphous solid dispersions by KinetiSol® Dispersing", *European Journal of Pharmaceutics and Biopharmaceutics*, 101:72-81, 2016b.

Lang et al., "Hot-melt extrusion—basic principles and pharmaceutical applications." *Drug Development and Industrial Pharmacy.* 40 (9): 1133-1155, 2014.

Lang et al., "Dissolution Enhancement of Itraconazole by Hot-Melt Extrusion Alone and the Combination of Hot-Melt Extrusion and Rapid Freezing—Effect of Formulation and Processing Variables", *Mol Pharm.*, 11(1):186-96, 2014b.

Lang et al., "Thin film freezing-template emulsion of itraconazole to improve the dissolution properties of poorly water-soluble drugs", *J Drug Deliv Sci Tec.*, 24(2):205-11, 2014a.

Laven et al, Effects of Dendrimer-Like Biopolymers on Physical Stability of Amorphous Solid Dispersions and Drug Permeability Across Caco-2 Cell Monolayers, AAPS PharSciTech 19(6):2459-2471, 2018.

Li et al., "Androgen receptor splice variants mediate enzalutamide resistance in castration-resistant prostate cancer cell lines", *Cancer research*, 73(2):483-9, 2013.

Li et al., "Multi-targeted therapy of cancer by niclosamide: A new application for an old drug", *Cancer letters*, 349(1):8-14, 2014.

Liu et al., "Formulation of a novel fixed dose combination of salmeterol xinafoate and mometasone furoate for inhaled drug delivery", *European journal of pharmaceutics and biopharmaceutics*, 96:132-42, 2015.

Liu et al., "Niclosamide enhances abiraterone treatment via inhibition of androgen receptor variants in castration resistant prostate cancer", *Oncotarget*, 7(22):32210. 2016.

Liu et al., "Niclosamide inhibits androgen receptor variants expression and overcomes enzalutamide resistance in castration-resistant prostate cancer", *Clinical Cancer Research*, 20(12):3198-3210, 2014.

Liu et al., "Niclosamide suppresses cell migration and invasion in enzalutamide resistant prostate cancer cells via Stat3-AR axis inhibition", *The Prostate*, 75(13):1341-53. 2015.

Lodagekar et al, "Formulation and evaluation of cyclodextrin complexes for improved anticancer activity of repurposed drug: Niclosamide", *Elsevier*, 212:252-259, 2019.

Luedeker et al., "Crystal Engineering of Pharmaceutical Co-crystals: "NMR Crystallography" of Niclosamide Co-crystals", *Crystal Growth & Design*, 16(6):3087-3100, 2016.

Matsubara et al., "Abiraterone Followed by Enzalutamide Versus Enzalutamide Followed by Abiraterone in Chemotherapy-naive Patients With Metastatic Castration-resistant Prostate Cancer", *Clinical Genitourinary Cancer*, 16(2):142-8, 2018.

Mook et al., "Structure-activity studies of Wnt/β-catenin inhibition in the Niclosamide chemotype: Identification of derivatives with improved drug exposure", *Bioorg. Med. Chem.*, 23:5829-5838, 2015.

Mostaghel et al., "Resistance to CYP17A1 Inhibition with Abiraterone in Castration-Resistant Prostate Cancer: Induction of Steroidogenesis and Androgen Receptor Splice Variants", *Clinical cancer research*, 17 (18): 5913-5925, 2011.

O'donnell et al., "Atmospheric freeze drying for the reduction of powder electrostatics of amorphous, low density, high surface area pharmaceutical powders", *Drug Dev Ind Pharm.*, 39(2):205-17, 2013.

Overhoff et al., "Effect of Stabilizer on the Maximum Degree and Extent of Supersaturation and Oral Absorption of Tacrolimus Made by Ultra-Rapid Freezing", *Pharm Res.*, 25(1):167-75, 2008.

Overhoff et al., "Novel ultra-rapid freezing particle engineering process for enhancement of dissolution rates of poorly water-soluble drugs", *European journal of pharmaceutics and biopharmaceutics*, 65(1):57-67, 2007b.

Overhoff et al., "Solid dispersions of itraconazole and enteric polymers made by ultra-rapid freezing", *Int J Pharmaceutics.*, 336(1):122-32, 2007a.

Overhoff et al., "Use of thin film freezing to enable drug delivery: A review", *J Drug Del Sci Tech.*, 19(2):89-98, 2009.

PCT International Search Report and Written Opinion issued in International Application No. PCT/US2021/025455, mailed Aug. 6, 2021.

Purvis et al., "Rapidly dissolving repaglinide powders produced by the ultra-rapid freezing process", *Aaps Pharmscitech.*, 8(3):E58, 2007.

Repka et al., "Pharmaceutical Applications of Hot-Melt Extrusion: Part II", *Drug Dev. Ind. Pharm.*, 33(10):1043-1057, 2007.

Rothan & Byrareddy., "The epidemiology and pathogenesis of coronavirus disease (COVID-19) outbreak", *J. Autoimmun.*, 109:102433, 2020.

Sanphui et al., "Pharmaceutical Cocrystals of Niclosamide", *Cryst. Growth Des.*, 12(9):4588-459, 2012.

(56) References Cited

OTHER PUBLICATIONS

Schweizer et al., "Correction: A phase I study of niclosamide in combination with enzalutamide in men with castration-resistant prostate cancer", *PloS one*, 13(6):e0198389, 2018.
Sinswat et al., "Nebulization of nanoparticulate amorphous or crystalline tacrolimus—single-dose pharmacokinetics study in mice", *European journal of pharmaceutics and biopharmaceutics*, 69(3):1057-66, 2008.
Tam et al., "Host-targeted niclosamide inhibits C. Dif cile virulence and prevents disease in mice without disrupting the gut microbiota", *Nat. Commun.*, 9:1-11. 2018.
Thakkar et al., "The immunogenicity of thin-film freeze-dried, aluminum salt-adjuvanted vaccine when exposed to different temperatures", *Human Vaccines Immunotherapeutics*, 13(4):936-46, 2017.
Tharmalingam et al., "Repurposing the anthelmintic drug niclosamide to combat *Helicobacter pylori*", *Sci. Rep.*, 8:3701, 2018.
Vincent et al., "Chloroquine is a potent inhibitor of SARS coronavirus infection and spread", *Virology. Journal.*, 2:69, 2005.
Vynckier et al., "Hot-melt co-extrusion: requirements, challenges and opportunities for pharmaceutical applications", *J. Pharm. Pharmacol.*, 66(2):167-179, 2014.
Wang et al., "Genetics and biology of prostate cancer", *Genes Development*, 32:1105-1140, 2018.
Wang et al., "In Vitro and In Vivo Performance of Dry Powder Inhalation Formulations: Comparison of Particles Prepared by Thin Film Freezing and Micronization", *Aaps Pharmscitech.*, 15(4):981-93, 2014.
Watts et al., "Characterization and pharmacokinetic analysis of tacrolimus dispersion for nebulization in a lung transplanted rodent model", *Int J Pharmaceutics.*, 384(1-2):46-52, 2010.
Wen et al., "Specific plant terpenoids and lignoids possess potent antiviral activities against severe acute respiratory syndrome coronavirus", *J. Med. Chem.*, 50:4087-4095, 2007.
Wu et al., "Inhibition of Severe Acute Respiratory Syndrome Coronavirus Replication by Niclosamide", *J. Antimicrob. Agents Chemother.*, 48, 2693-2696, 2004.
Wu et al., Synergistic effect on thermal behavior during co-pyrolysis of lignocellulosic biomass model components blend with bituminous coal, *Bioresource Technology*, 169:220-228,2014.
Xie et al, "Octenysuccinate hydroxypropyl phytoglycogen enhances the solubility and in-vitro antitumor efficacy of niclosamide", International Journal of Pharmaceutics, 535:157-163, 2018.
Xu et al., "Broad Spectrum Antiviral Agent Niclosamide and Its Therapeutic Potential", *ACS Infect. Dis.*, 6(5):909-915, 2020.
Yang et al, "In vitro characterization and pharmacokinetics in mice following pulmonary delivery of itraconazole as cyclodextrin solubilized solution", *European Journal of Pharmaceutical Sciences*, 39:336-347, 2010.
Ying et al, "Octenylsuccinate hydroxypropyl phytoglycogen enhances the solubility and in-vitro antitumor efficacy of niclosamide", *International Journal of Pharmaceutics, Elsevier*, 535(1):157-163, (2017).
Zhang et al., "Formulation and delivery of improved amorphous fenofibrate solid dispersions prepared by thin film freezing", *European journal of pharmaceutics and biopharmaceutics*, 82(3):534-44, 2012.
Zhang et al., "Androgen Receptor Variants Occur Frequently in Castration Resistant Prostate Cancer Metastases", *PloS one*; 6(11):e27970, 2011.

* cited by examiner

PHARMACEUTICAL COMPOSITIONS OF NICLOSAMIDE

This application claims the benefit of priority to U.S. Provisional Application No. 63/003,793, filed on Apr. 1, 2020, the entire contents of which are hereby incorporated by reference.

BACKGROUND

1. Field

The present disclosure relates generally to the field of pharmaceuticals and pharmaceutical manufacture. More particularly, it concerns compositions and methods of preparing a pharmaceutical composition comprising niclosamide.

2. Description of Related Art

The WHO has declared the Coronavirus Disease 2019 (COVID-19) outbreak a pandemic (WHO Director-General's opening remarks at the Mission briefing on COVID-19-12 Mar. 2020. www.who.int/dg/speeches/detail/who-director-general-s-opening-remarks-at-the-mission-briefing-on-covid-19-12-march-2020). This virus is related to other coronaviruses that have created pandemics called the Severe Acute Respiratory Syndrome (SARS-CoV) in 2002 and the Middle East Respiratory Syndrome (MERS-CoV) in 2012 (Wu et al., 2004; Peeri et al., 2020). Currently, this COVID-19 has killed more people than the others two mentioned pandemics together (Gurwitz, 2020). This COVID-19 has been named as SARS-CoV-2 because its share near 80% of the genome with the SARS-CoV (Yan et al., 2020). Moreover, it has been reported that both viruses interact with similar affinity with angiotensin-converting enzyme 2 (ACE2), a protein that works as an entry receptor (Ahmed et al., 2020; Walls et al., 2020).

Unfortunately, there are no specific drugs for coronaviruses (Walls et al., 2020; Tortoric et al., 2019). The present strategy in drug discovery has been the test of drugs previously used in SARS and MERS (Wang et al., 2020). Recently, the drug chloroquine was successful against an in-vitro isolate COVID-19 (Vero E6 cells) with an $IC_{50}$ of 1.13 µM. The mechanism was attributed to an increased endosomal pH, one of the same mechanisms reported for another drug called niclosamide (Jurgeit et al., 2012; Vincent et al., 2005; Wang et al., 2018). In Vero cells infected by SARS-CoV (2002 pandemic), the reported $IC_{50}$ of chloroquine is 4.4 µM, yet niclosamide inhibits viral replication with an $IC_{50}$<0.1 µM (Wen et al., 2007). In a separate experiment, SARS-CoV replication was completely inhibited using niclosamide at concentrations between 1.56-3.12 µM (Wu et al., 2004). For these reasons, niclosamide has been proposed as a candidate for this COVID-19 pandemic and has recently shown an $IC_{50}$ of 0.28 µM (Xu et al., 2020; Jeon et al., 2020).

Niclosamide has been used for 60 years, it is an FDA approved anthelmintic drug that is listed as an Essential Medicine by the WHO (Barbosa et al., 2019). Niclosamide has been proposed as a candidate for repurposing as a multi-targeted cancer therapy, broad-spectrum antiviral, and antibacterial, among several others (Xu et al., 2020; Li et al., 2014; Chen et al., 2018; Tam et al., 2018). It seems that the main feature that allows all those effects are the physical chemistry of the molecule itself instead of specific ligand-receptor interactions (Fonseca et al., 2012). Niclosamide is well known for its protonophoric activity, in other words, the capability of transporting protons through membranes and disrupting pH gradients that regulate several key signaling pathways (Jurgeit et al., 2012; Xu et al., 2020; Li et al., 2014; Chen et al., 2018; Tam et al., 2018; Fonseca et al., 2012; Circu et al., 2016; Ippolito et al., 2016; Mook et al., 2015; Tharmalingam et al., 2018). In CoVs, niclosamide has inhibited MERS-CoV replication more than 1000 fold by modifying pathways related to the proteasome and autophagy mechanisms (Xu et al., 2020; Gassen et al., 2019). This feature can make niclosamide a host-directed broad-spectrum antiviral (Chen et al., 2018). The main limitation of these studies is that they were conducted using DMSO as a solvent.

Niclosamide has been effective in SARS-CoV (Wu et al., 2014; Wen et al., 2007) and MERS-CoV (Wu et al., 2014; Wen et al., 2007; Gassen et al., 2019). It has been proposed that niclosamide can be a therapeutic option for SARS-CoV-2 (Xu et al., 2020). As stated earlier, SARS-Cov-2 targets ACE2 which is not only expressed in the lungs (main entry) but also in intestine, kidney, and blood vessels (Fang et al., 2020). This increases the risk in populations with diabetes and hypertension that normally upregulate those receptors (Fang et al., 2020). Some patients undergo gastrointestinal symptoms similar to SARS-CoV and MERS-CoV and cardiac problems (Rothan & Byrareddy, 2020). SARS-CoV can replicated in the intestinal lumen and niclosamide orally could be helpful.

While niclosamide has been used for treating several indications, the current formulations suffer from low solubility and have not been shown in a formulation useful for delivery via inhalation to the lungs. Therefore, there remains a need for improved formulations of niclosamide for potential treatment of numerous indications.

SUMMARY OF THE INVENTION

The present disclosure provides pharmaceutical compositions comprising niclosamide for administration orally or via inhalation. Without wishing to be bound by any theory, these compositions may have one or more advantageous properties such as higher drug loading, maintenance of a therapeutically effective dose, or other properties such as ability to more effectively deliver the drug to the target organ. In some embodiments, the present disclosure provides pharmaceutical compositions comprising:

The present disclosure provides pharmaceutical compositions comprising niclosamide for administration orally or via inhalation. Without wishing to be bound by any theory, these compositions may have one or more advantageous properties such as higher drug loading, maintenance of a therapeutically effective dose, or other properties such as ability to more effectively deliver the drug to the target organ. In some embodiments, the present disclosure provides pharmaceutical compositions comprising:

(A) an active agent, wherein the active agent is niclosamide, a pharmaceutically acceptable salt thereof, a hydrate, or a co-crystal thereof; and (B) a pharmaceutically acceptable polymer;

wherein the pharmaceutical composition is formulated for administration orally and the therapeutic agent is in an amorphous form as an amorphous solid dispersion.

In some embodiments, the composition has been formulated through hot melt extrusion. In further embodiments, the hot melt extrusion is conducted at a temperature from about 100° C. to about 240° C. In still further embodiments, the hot melt extrusion is conducted at a temperature from about 150° C. to about 210° C., such as about 180° C. In some embodiments, the pharmaceutical composition comprises from about 5% w/w to about 90% w/w of the active agent. In further embodiments, the pharmaceutical composition comprises from about 10% w/w to about 80% w/w of the active agent. In still further embodiments, the pharmaceutical composition comprises from about 20% w/w to about 60% w/w of the active agent. In yet further embodiments, the pharmaceutical composition comprises from about 30% w/w to about 50% w/w of the active agent, such as about 40% w/w of the active agent. In some embodiments, the pharmaceutical composition comprises from about 40% w/w to about 95% w/w of the pharmaceutically acceptable polymer. In further embodiments, the pharmaceutical composition comprises from about 40% w/w to about 80% w/w of the pharmaceutically acceptable polymer. In still further embodiments, the pharmaceutical composition comprises from about 50% w/w to about 70% w/w of the pharmaceutically acceptable polymer, such as about 60% w/w of the pharmaceutically acceptable polymer. In some embodiments, the pharmaceutical composition comprises from about 70% w/w to about 90% w/w of the pharmaceutically acceptable polymer.

In some embodiments, the pharmaceutically acceptable polymer is selected from the group consisting of a neutral non-cellulosic polymer, an ionizable non-cellulosic polymer, an ionizable cellulosic polymer, a neutral cellulosic polymer, and any combination thereof. In some embodiments, the neutral non-cellulosic polymer is selected from the group consisting of polyvinyl pyrrolidone, polyvinyl alcohol, copovidone, and poloxamer. In further embodiments, the pharmaceutically acceptable polymer is a copovidone polymer, such as Kollidon 30® (polyvinylpyrrolidone). In some embodiments, the ionizable non-cellulosic polymer is selected from the group consisting of carboxylic acid, functionalized polyacrylate, and polymethacrylate. In further embodiments, the pharmaceutically acceptable polymer is a graft copolymer of polyvinyl caprolactam-polyvinyl acetate-polyethylene glycol, such as SoluPlus® (polyvinyl caprolactampolyvinyl acetate-polyethylene glycol graft copolymer). In some embodiments, the pharmaceutically acceptable polymer is a copolymer of polyvinyl pyrrolidone and polyvinyl acetate, such as VA64® (copovidone, vinylpyrrolidone-vinyl acetate).

In some embodiments, the pharmaceutical composition further comprises an excipient. In further embodiments, the excipient is a surfactant or emulsifier. In still further embodiments, the excipient is a derivative of polysorbate. In yet further embodiments, the derivative of polysorbate is a Tween® compound (polyethylene glycol sorbitan monolaurate). In some embodiments, the excipient is a PEGylated version of vitamin E. In further embodiments, the PEG group in the PEGylated version of vitamin E has a molecular weight from about 400 to about 4000, such as TPGS 1000. In some embodiments, the excipient is a composition of two or more excipients. In further embodiments, the excipient is two or more surfactants or emulsifiers. In still further embodiments, the excipient is a mixture of a derivative of polysorbate and a monoglyceride, a diglyceride, or a triglyceride. In yet further embodiments, the derivative of polysorbate is a Tween® compound (polyethylene glycol sorbitan monolaurate). In some embodiments, the pharmaceutical composition is a mixture of a monoglyceride and diglyceride. In further embodiments, the mixture of monoglycerides and diglyceride is a mixture of medium chain fatty acid monoglycerides and medium chain fatty acids diglycerides. In still further embodiments, the mixture of monoglycerides and diglycerides is a Capmul® composition (a group of monoglycerides or diglycerides). In some embodiments, the excipient is a triglyceride. In further embodiments, the triglyceride is a medium chain triglyceride. In further embodiments, the triglyceride is a Captex® compound (decanoic acid; octanoic acid; propane-1,2,3-triol).

In some embodiments, the pharmaceutical composition comprises from about 1% w/w to about 20% w/w of an excipient. In further embodiments, the pharmaceutical composition comprises from about 1% w/w to about 10% w/w of an excipient, such as about 5% w/w of an excipient. In some embodiments, the excipient is a mixture of three excipients present in a ratio from about 1:0.1:0.1 to about 0.1:1:1. In further embodiments, the ratio is from about 1:0.25:0.25 to about 0.25:1:1, such as about 2:1:1.

In some embodiments, the composition is substantially free of any of liposomes or micelles. In some embodiments, the composition is substantially free of any other compounds. In some embodiments, the composition is essentially free of any other compounds. In some embodiments, the composition is entirely free of any other compounds.

In other aspects, the present disclosure provides pharmaceutical composition comprising:

(A) an active agent wherein active agent is niclosamide, a pharmaceutically acceptable salt thereof, a hydrate, or a co-crystal thereof;

wherein the pharmaceutical composition is formulated for administration via inhalation and the pharmaceutical composition comprises less than 10% amorphous material. In further embodiments, the pharmaceutical composition is a dry powder. In still further embodiments, the active agent is substantially present as the crystalline form. In yet further embodiments, the active agent is essentially present as the crystalline form. In further embodiments, the active agent is entirely present as the crystalline form. In still further embodiments, the composition is essentially free of amorphous particles as determined by x-ray diffraction or differential scanning calorimetry.

In some embodiments, the pharmaceutical composition comprises less than 5% amorphous material. In further embodiments, the pharmaceutical composition comprises less than 1% amorphous material. In still further embodiments, the pharmaceutical composition comprise less than 0.1% amorphous material. In yet further embodiments, the pharmaceutical composition comprise no amorphous material. In some embodiments, the pharmaceutical composition comprises a single active agent. In further embodiments, the single active agent is niclosamide or a pharmaceutically acceptable salt or co-crystal thereof. In some embodiments, the pharmaceutically composition is substantially free of any sugars, lubricants, antistatic agents, anti-adherents, glidants, amino acids, peptides, surfactants, lipids, and phospholipids. In further embodiments, the pharmaceutically composition is essentially free of any sugars, lubricants, antistatic agents, anti-adherents, glidants, amino acids, peptides, surfactants, lipids, and phospholipids. In further embodiments, the pharmaceutical composition is entirely free of any sugars, lubricants, antistatic agents, anti-adherents, glidants, amino acids, peptides, surfactants, lipids, and phospholipids. In some embodiments, the pharmaceutically composition is substantially free of any added excipients. In some embodiments, the pharmaceutical composition is essentially free of any added excipients. In further embodiments, the pharmaceutical composition is entirely free of any added excipients. In some embodiments, the pharmaceutically composition is substantially free of any excipients. In further embodiments, the pharmaceutical composition is essentially free of any excipients. In still further embodiments, the pharmaceutical composition is entirely free of any excipients.

In some embodiments, the pharmaceutical composition has been micronized. In further embodiments, the micronized pharmaceutical composition comprises a plurality of particles containing the active agent. In still further embodiments, the particles have a laser diffraction median particle diameter of about 0.5 µm to about 10 µm. In still further embodiments, the particles have laser diffraction median particle diameter of about 1.5 µm to about 5 µm. In yet further embodiments, the particles have laser diffraction median particle diameter of about 2.5 µm to about 3.5 µm. In some embodiments, the particles comprise at least 90% of the active agent. In further embodiments, the particles comprise at least 95% of the active agent. In still further embodiments, the particles comprise at least 99% of the active agent. In yet further embodiments, the particles comprise 100% of the active agent. In some embodiments, the composition comprises at least 95% of the active agent. In further embodiments, the composition comprises at least 99% of the active agent. In still further embodiments, the composition comprises at least 100% of the active agent. In some embodiments, the composition is formulated in saline. In further embodiments, the saline is 0.9% w/v sodium chloride. In some embodiments, the composition is essentially free of any micelles or liposomes.

In some embodiments, the pharmaceutical composition is produced by jet milling. In further embodiments, the pharmaceutical composition is produced by air jet milling. In some embodiments, the pharmaceutical composition is formulated as a brittle matrix particle. In further embodiments, the pharmaceutical composition comprises an excipient. In still further embodiments, the excipient is a carbohydrate, such as lactose or mannose. In other embodiments, the excipient is a cyclodextrin such as a sulfobutyl ether β-cyclodextrin. In some embodiments, the pharmaceutical composition comprises an amount of excipient from about 25% w/w to about 95% w/w. In some embodiments, the amount of excipient is from about 40% w/w to about 90% w/w. In some embodiments, the amount of excipient is from about 60% w/w to about 85% w/w.

In some embodiments, the pharmaceutical compositions further comprise an additional excipient. In some embodiments, the additional excipient is a flowing agent such as magnesium stearate. In other embodiments, the additional excipient is a phospholipid such as 1,2-dioctadecanoyl-sn-glycero-3-phosphocholine. In other embodiments, the additional excipient is a hydrophobic amino acid such as leucine. In some embodiments, the pharmaceutical composition comprises an amount of the additional excipient from about 0.1% w/w to about 25% w/w. In some embodiments, the amount of the additional excipient is from about 0.25% w/w to about 20% w/w. In some embodiments, the amount of the additional excipient is from about 0.25% w/w to about 5% w/w. In some embodiments, the amount of the additional excipient is from about 5% w/w to about 20% w/w.

In some embodiments, the pharmaceutical composition comprises a specific surface area of greater than 10 g/m$^2$. In some embodiments, the excipient and the active agent are present in particles. In further embodiments, the particles contain excipient and active agent which are phase separated. In some embodiments, the particles have a median mass aerodynamic diameter from about 1.5 µm to about 10 µm. In further embodiments, the median mass aerodynamic diameter is from about 2.0 µm to about 8 µm. In still further embodiments, the median mass aerodynamic diameter is from about 2.0 µm to about 4 µm. In some embodiments, the pharmaceutical composition is loaded into an inhaler. In further embodiments, the inhaler is a dry powder inhaler, a metered dose inhaler, a single dose inhaler, a multi-dose inhaler, or a pressurized metered dose inhaler. In some embodiments, the pharmaceutical composition is formulated for use in a nebulizer. In further embodiments, the nebulizer is a jet nebulizer or a vibrating mesh nebulizer.

In some embodiments, the active agent is niclosamide. In other embodiments, the active agent is a pharmaceutically acceptable salt of niclosamide. In further embodiments, the pharmaceutically acceptable salt of niclosamide is an ethanolamine salt or a piperazine salt of niclosamide. In some embodiments, the active agent is anhydrous niclosamide. In some embodiments, the active agent is a hydrate of niclosamide. In further embodiments, the active agent is niclosamide monohydrate. In some embodiments, the active agent is a co-crystal of niclosamide. In further embodiments, the co-crystal of niclosamide is a co-crystal of niclosamide and 2-aminothazole, a co-crystal of niclosamide and benzamide, a co-crystal of niclosamide and isoniazid, a co-crystal of niclosamide and acetamide, a co-crystal of niclosamide and caffeine, a co-crystal of niclosamide and urea, a co-crystal of niclosamide and p-aminobenzoic acid, a co-crystal of niclosamide and theophylline, a co-crystal of niclosamide and nicotinamide, or a co-crystal of niclosamide and isonicotinamide.

In some embodiments, the pharmaceutical composition is formulated as unit dose. In further embodiments, the unit dose is formulated for oral administration as a hard or soft capsule, a tablet, a syrup, a suspension, an emulsion, a solution, or a wafer. In some embodiments, the active agent is present in an amount from about 100 mg to about 5 g. In further embodiments, the active agent is present in an amount from about 500 mg to about 2 g. In some embodiments, the unit dose is formulated for inhalation as a capsule, cartridge, or blister. In further embodiments, the capsule, cartridge, or blister is formulated for use with an inhaler. In some embodiments, the active agent is present in an amount from about 100 μg to about 50 mg. In further embodiments, the active agent is present in an amount from about 250 μg to about 20 mg. In some embodiments, the pharmaceutical composition is present in a container which blocks UV light.

In some embodiments, the composition further comprises a second active agent. In further embodiments, the second active agent is anti-inflammatory. In still further embodiments, the second active agent is clofazimine. In yet further embodiments, the second active agent is anti-microbial, such as chloroquine, hydroxychloroquine, thalidomide, plasminogen, colistin, or polymyxin B. In other embodiments, the second active agent is chemotherapeutic agent, such as abiraterone, enzalutamide, or bicalutamide. In still other embodiments, the second active agent is a protein.

In still other aspects, the present disclosure provides inhalers comprising a pharmaceutical composition of the present disclosure. In further embodiments, the inhaler has a dispersion energy from about 0.5 bar to 5 bar. In still further embodiments, the dispersion energy is 1, 2, or 3 bar.

In yet other aspects, the present disclosure provides methods of preparing a pharmaceutical composition of the present disclosure comprising:

(A) obtaining a pharmaceutically acceptable polymer and an active agent, wherein the active agent is niclosamide, a pharmaceutically acceptable salt thereof, or a co-crystal thereof; and (B) subjecting the pharmaceutically acceptable polymer and the active agent to a hot melt extruder to obtain a pharmaceutical composition.

In some embodiments, the pharmaceutically acceptable polymer and the active agent are extruded at a temperature from about temperature from about 100° C. to about 240° C. In further embodiments, the temperature is from about 150° C. to about 210° C., such as about 180° C.

In other aspects, the present disclosure provides methods of preparing a pharmaceutical composition according of the present disclosure comprising:
(A) obtaining an active agent, wherein the active agent is niclosamide, a pharmaceutically acceptable salt thereof, or a co-crystal thereof;
(B) subjecting the active agent to a jet mill to obtain a pharmaceutical composition.

In some embodiments, the jet mill is an air jet mill. In further embodiments, the jet mill further comprises a cyclone. In still further embodiments, the jet mill is set to a grind pressure from about 25 psi to about 150 psi. In yet further embodiments, the grind pressure is from about 50 psi to about 100 psi, such as about 80 psi. In some embodiments, the jet mill is set to a feed pressure from about 25 psi to about 150 psi. In further embodiments, the feed pressure is from about 50 psi to about 100 psi, such as about 80 psi. In some embodiments, the feed rate is less than 1 g/min. In further embodiments, the feed rate is from about 0.1 g/min to about 1 g/min. In still further embodiments, the feed rate is from about 0.5 g/min to about 1 g/min.

In still other aspects, the present disclosure provides methods of preparing a pharmaceutical composition of the present disclosure comprising:
(A) dissolving an active agent, wherein the active agent is niclosamide, a pharmaceutically acceptable salt thereof, or a co-crystal thereof, in a solvent to obtain a pharmaceutical mixture;
(B) applying the pharmaceutical mixture to a surface at a temperature below 0° C. to obtain a frozen pharmaceutical mixture; and
(C) collecting the frozen pharmaceutical mixture and drying the frozen pharmaceutical mixture to obtain a pharmaceutical composition.

In some embodiments, the solvent is an organic solvent, such as 1,4-dioxane. In some embodiments, the methods further comprise admixing the active agent with an excipient, wherein the excipient is dissolved in a second solvent, to obtain the pharmaceutical mixture. In some embodiments, the second solvent is water. In some embodiments, the pharmaceutical mixture is admixed until the pharmaceutical mixture is clear. In some embodiments, the pharmaceutical mixture is applied at a feed rate from about 0.5 mL/min to about 5 mL/min. In further embodiments, the feed rate is from about 1 mL/min to about 3 mL/min, such as about 2 mL/min. In some embodiments, the pharmaceutical mixture is applied with a needle. In further embodiments, the needle is a 19 gauge needle. In some embodiments, the pharmaceutical mixture is applied from a height from about 2 cm to about 50 cm. In further embodiments, the height is from about 5 cm to about 20 cm, such as about 10 cm. In some embodiments, the temperature is from about 0° C. to −100° C. In further embodiments, the temperature is from about −20° C. to about −90° C., such as about −80° C. In some embodiments, the surface is a rotating surface. In further embodiments, the surface is rotating at a speed from about 50 rpm to about 500 rpm. In still further embodiments, the surface is rotating at a speed from about 100 rpm to about 400 rpm, such as about 200 rpm.

In some embodiments, the frozen pharmaceutical composition is dried by lyophilization. In further embodiments, the frozen pharmaceutical composition is dried at a first reduced pressure. In still further embodiments, the first reduced pressure is from about 10 mTorr to 500 mTorr. In yet further embodiments, the first reduced pressure is from about 50 mTorr to about 250 mTorr, such as about 100 mTorr. In some embodiments, the frozen pharmaceutical composition is dried at a first reduced temperature. In further embodiments, the first reduced temperature is from about 0° C. to −100° C. In still further embodiments, the first reduced temperature is from about −20° C. to about −60° C., such as about −40° C. In some embodiments, the frozen pharmaceutical composition is dried for a first time period from about 3 hours to about 36 hours. In further embodiments, the first time period is from about 6 hours to about 24 hours, such as about 20 hours.

In some embodiments, the frozen pharmaceutical composition is dried a second time. In further embodiments, the frozen pharmaceutical composition is dried a second time at a second reduced pressure. In still further embodiments, the second reduced pressure is from about 10 mTorr to 500 mTorr. In yet further embodiments, the second reduced pressure is from about 50 mTorr to about 250 mTorr, such as about 100 mTorr. In some embodiments, the frozen pharmaceutical composition is dried a second time at a second reduced temperature. In further embodiments, the second reduced temperature is from about 0° C. to 30° C. In still further embodiments, the second reduced temperature is from about 10° C. to about 30° C., such as about 25° C. In some embodiments, the frozen pharmaceutical composition is dried for a second time for a second time period from about 3 hours to about 36 hours. In further embodiments, the second time period is from about 6 hours to about 24 hours, such as about 20 hours.

In yet other aspects, the present disclosure provides methods of preparing a pharmaceutical composition comprising:
(A) admixing an active agent with saline to form a pharmaceutical mixture;
(B) homogenizing the pharmaceutical mixture to obtain the pharmaceutical composition.

In some embodiments, the active agent and the saline are admixed through sonication. In further embodiments, the sonication is ultrasonication. In some embodiments, the homogenization is carried out with a rotor stator homogenizer. In further embodiments, the rotor stator homogenizer is a saw-tooth bladed rotor stator homogenizer. In some embodiments, the pharmaceutical mixture is homogenized at a speed from about 5,000 rpm to about 50,000 rpm. In further embodiments, the speed is from about 20,000 rpm to about 40,000 rpm, such as about 30,000 rpm. In some embodiments, the methods further comprise centrifuging the pharmaceutical composition. In further embodiments, the pharmaceutical composition is centrifuged at a speed from about 50 g to about 200 g. In still further embodiments, the speed is from about 100 g to about 150 g, such as about 118 g. In some embodiments, the methods further comprise sonicating the pharmaceutical composition. In some embodiments, the methods further comprise admixing a second therapeutic agent to the pharmaceutical mixture. In further embodiments, the second therapeutic agent is a protein. In still further embodiments, the second therapeutic agent is a therapeutic protein.

In other aspects, the present disclosure provides pharmaceutical compositions prepared according to the methods of the present disclosure.

In still other aspects, the present disclosure provides methods of treating a disease or disorder in a patient comprising administering a pharmaceutical composition of the present disclosure to the patient in a therapeutically effective amount. Similarly, the present disclosure also provides compositions for use in the treatment of a disease or disorder. In some embodiments, the pharmaceutical composition is administered to the patient orally such as when the pharmaceutical composition is administered orally to the patient as a hard or soft capsule, a tablet, a syrup, a suspension, an emulsion, a solution, or a wafer. In other embodiments, the pharmaceutical composition is administered to the patient via inhalation. In further embodiments, the disease or disorder is a microbial infection. In still further embodiments, the microbial infection is a viral infection. In yet further embodiments, the viral infection is an infection of a coronavirus. In further embodiments, the coronavirus is MERS-Cov, SARS-Cov1, or SARS-Cov2 (COVID-19). In other embodiments, the viral infection is influenza. In still other embodiments, the viral infection is Zika. In yet other embodiments, the microbial infection is hemorrhagic fever, such as Ebola and Lassa fever. In other embodiments, the viral infection is HIV. In some embodiments, the HIV presents with tuberculosis. In yet other embodiments, the microbial infection is a flatworm infection. In further embodiments, the flatworm infection is Schistosomiasis or complication from Schistosomiasis. In still further embodiments, the Schistosomiasis is acute pulmonary Schistosomiasis. In other embodiments, the complication from schistosomiasis is schistosomiasis associated pulmonary hypertension. In other embodiments, the microbial infection is bacterial infection. In further embodiments, the bacterial infection is an infection of enterococci, *Pseudomonas aeruginosa*, *Staphylococcus aureus*, or *Clostridium difficile*. In still further embodiments, the bacterial infection is an infection of a bacteria resistant to one or more antibiotics. In yet further embodiments, the infection is an infection of a bacteria resistant to vancomycin or methicillin.

In other embodiments, the disease or disorder is cancer. In further embodiments, the cancer is lung cancer, glioblastoma, or prostate cancer. In still further embodiments, the prostate cancer is a castration resistant prostate cancer. In other embodiments, the disease or disorder is diabetes. In some embodiments, the methods further comprise a second active agent. In further embodiments, the second active agent is an anti-inflammatory, such as clofazimine. In other embodiments, the second active agent is anti-microbial, such as chloroquine, hydroxychloroquine, thalidomide, plasminogen, colistin, or polymyxin B. In still other embodiments, the second active agent is chemotherapeutic agent, such as abiraterone, enzalutamide, or bicalutamide. In some embodiments, the active agent is inhaled to the lungs. In further embodiments, the active agent is inhaled into the lungs and the stomach.

In yet other aspects, the present disclosure provides methods of reducing lung inflammation in a patient comprising administering a pharmaceutical composition of the present disclosure to the patient in a therapeutically effective amount. Similarly, the present disclosure provides compositions for use in the reduction of lung inflammation. In some embodiments, the pharmaceutical composition is administered to the patient orally such as when the pharmaceutical composition is administered orally to the patient as a hard or soft capsule, a tablet, a syrup, a suspension, an emulsion, a solution, or a wafer. In other embodiments, the pharmaceutical composition is administered to the patient via inhalation. In some embodiments, the lung inflammation is associated with a viral infection. In some embodiments, the pharmaceutical composition is administered more than once.

In other aspects, the present disclosure provides pharmaceutical compositions comprising:

(A) an active agent, wherein the active agent is niclosamide, a pharmaceutically acceptable salt thereof, a hydrate, or a co-crystal thereof; and (B) saline;

wherein the pharmaceutical composition is formulated for use in a nebulizer, the active agent is micronized with a median mass aerodynamic diameter is from about 2.0 μm to about 4.0 μm, and the concentration of the active agent is from about 2 mg/mL to about 6 mg/mL.

In still other aspects, the present disclosure provides pharmaceutical compositions comprising:

(A) an active agent, wherein the active agent is niclosamide, a pharmaceutically acceptable salt thereof, a hydrate, or a co-crystal thereof; and (B) a pharmaceutically acceptable polymer, wherein the pharmaceutically acceptable polymer is a copolymer of polyvinyl pyrrolidone and polyvinyl acetate;

wherein the pharmaceutical composition is formulated for oral administration and the active agent is present in the amorphous form and is phase separated in the pharmaceutical composition.

In yet other aspects, the present disclosure provides pharmaceutical compositions comprising:

(A) an active agent, wherein the active agent is niclosamide, a pharmaceutically acceptable salt thereof, a hydrate, or a co-crystal thereof; and (B) mannitol;

wherein the pharmaceutical composition is formulated for administration via inhalation and has a median mass aerodynamic diameter from about 1.5 μm to about 4 μm.

In other aspects, the present disclosure provides pharmaceutical compositions comprising:

(A) an active agent, wherein the active agent is niclosamide, a pharmaceutically acceptable salt thereof, a hydrate, or a co-crystal thereof;

wherein the pharmaceutical composition is formulated for administration via inhalation, comprises at least 99.9% of the active agent, and the pharmaceutical composition is formulated as particles wherein the particles have a laser diffraction median mass aerodynamic diameter from about 1.5 μm to about 4.0 μm.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 8:
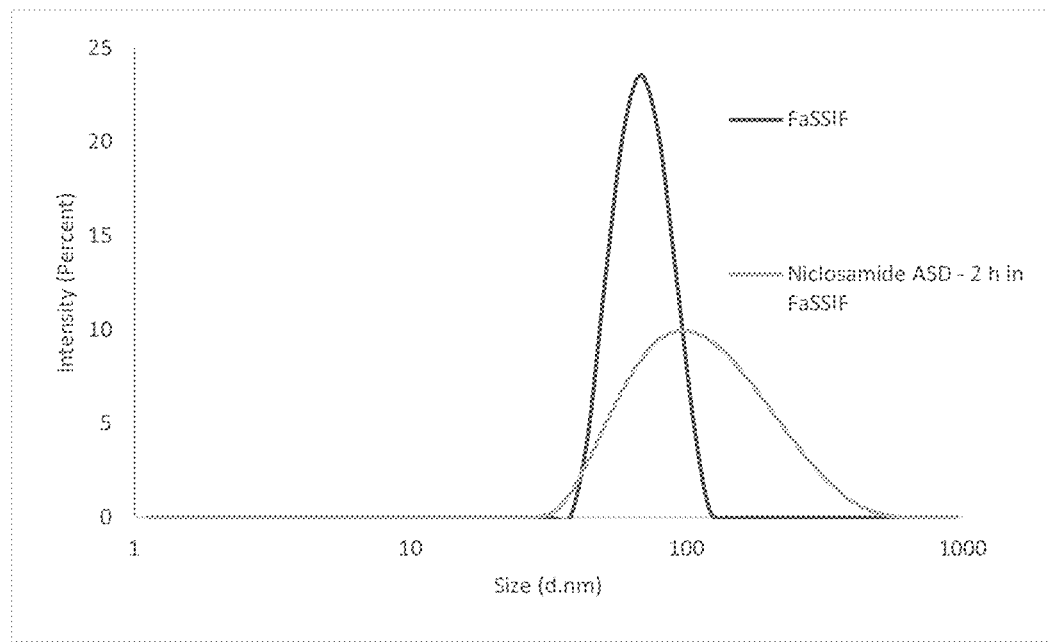

FIG. 8 shows the dissolution profile of niclosamide ASD, its physical mixture (PM), and niclosamide anhydrate in FaSSIF media. The samples were taken and passed through 0.2 μm filters. The particle size distribution of niclosamide ASD after 2 h in FaSSIF and a FaSSIF control.

Figure 9:
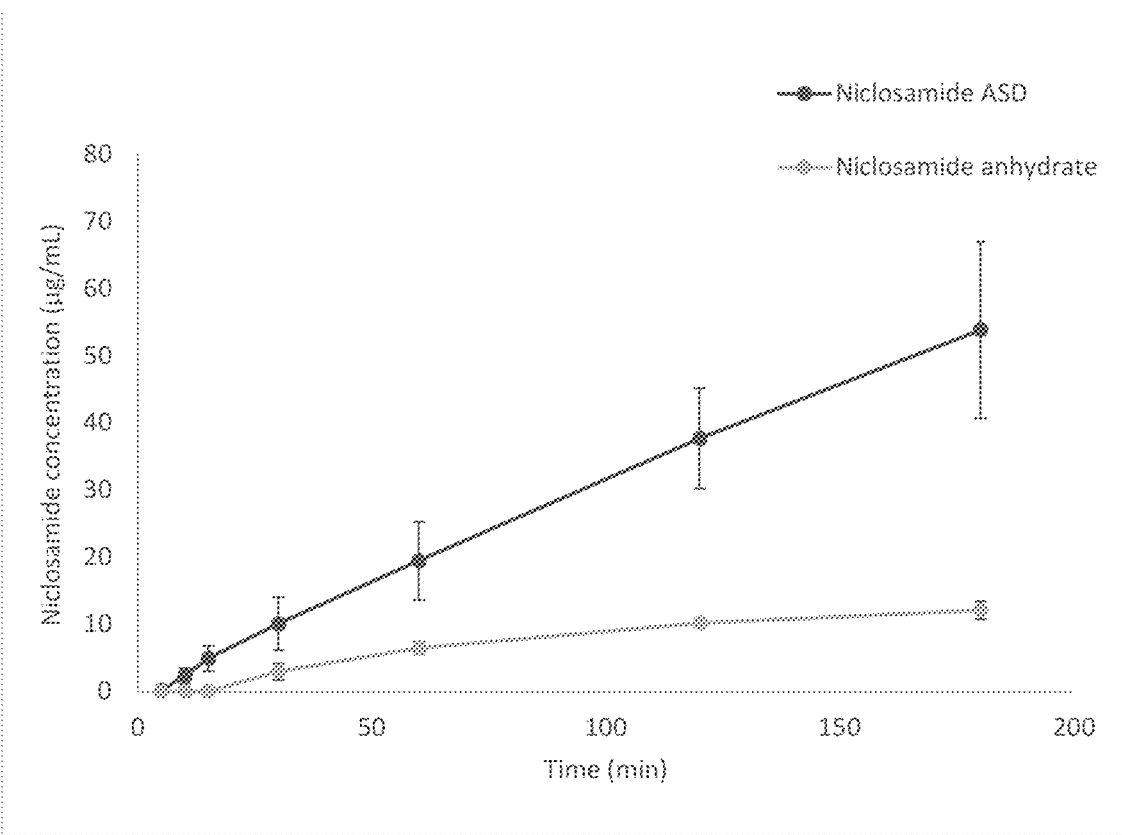

FIG. 9 shows the diffusion profiles of niclosamide ASD and niclosamide anhydrate. The donor and receiver cells were filled with FaSSIF and decanol, respectively.

Figure 10:
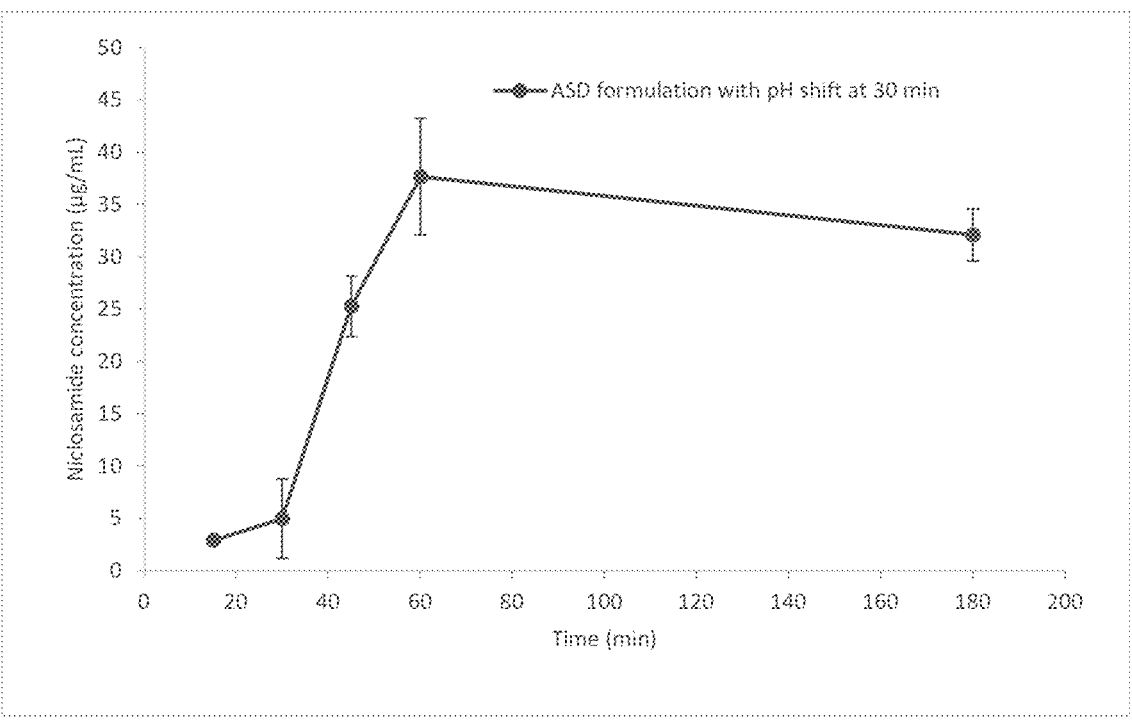

FIG. 10 shows the pH-shift dissolution test of niclosamide ASD.

Figure 11:
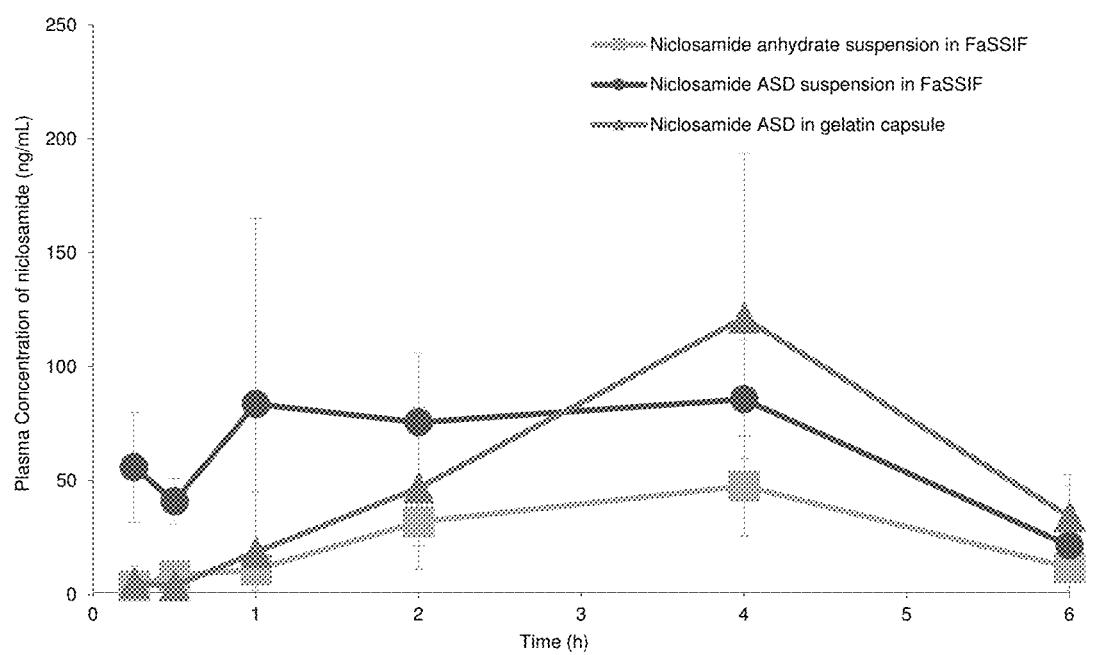

FIG. 11 shows the pharmacokinetic profiles (in rats) of niclosamide anhydrate suspended in FaSSIF, niclosamide ASD suspended in FaSSIF, and niclosamide ASD in capsules (n=5).

Figure 12:
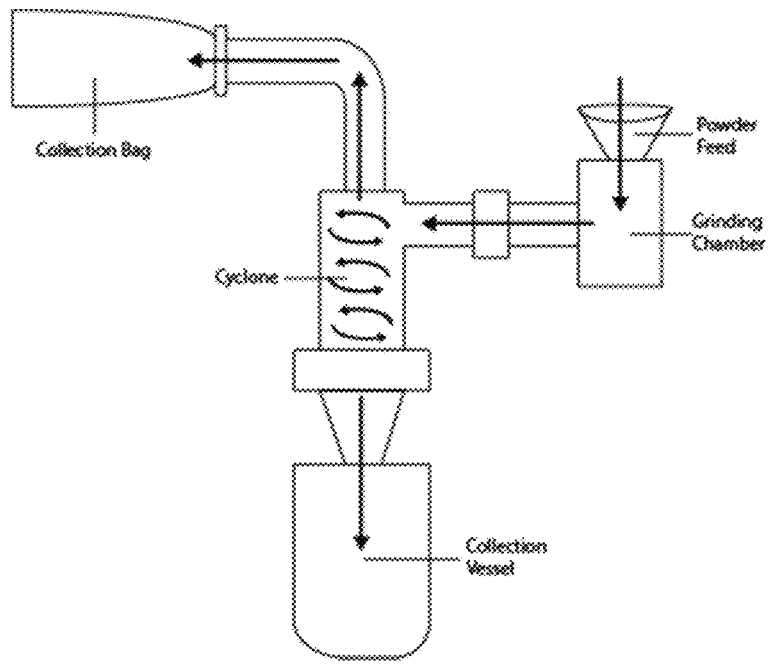

FIG. 12 shows a model of a jet milling apparatus.

Figure 13:
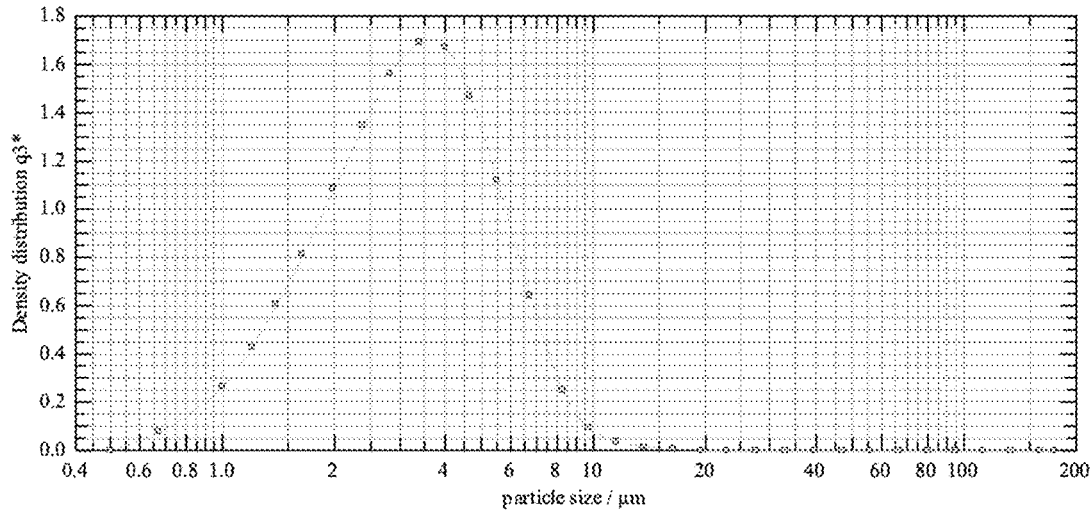

FIG. 13 shows the particle distribution for the micronized particles by jet milling.

Figure 14:
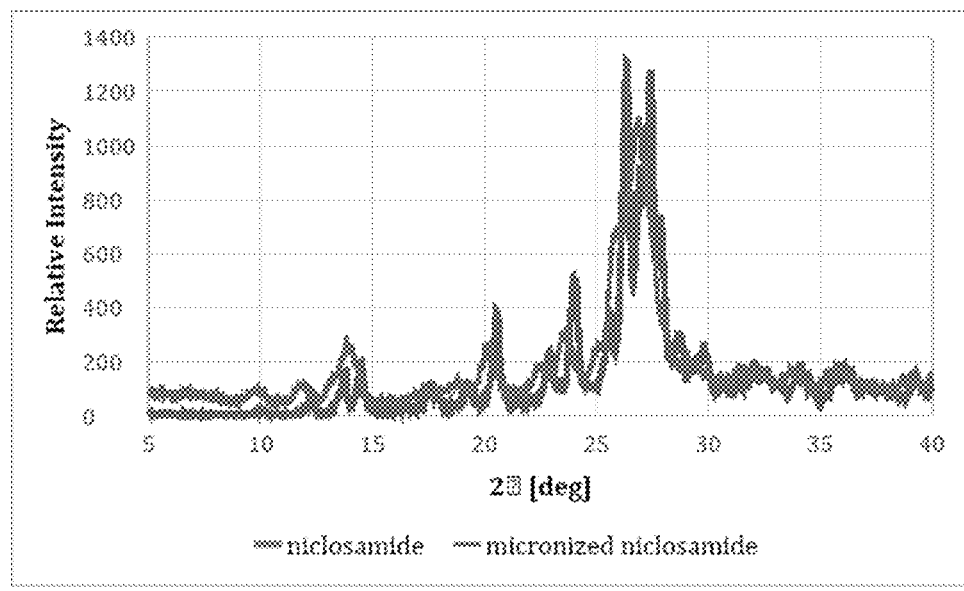

FIG. 14 shows the powder x-ray diffraction of crystalline niclosamide and micronized niclosamide.

Figure 15:
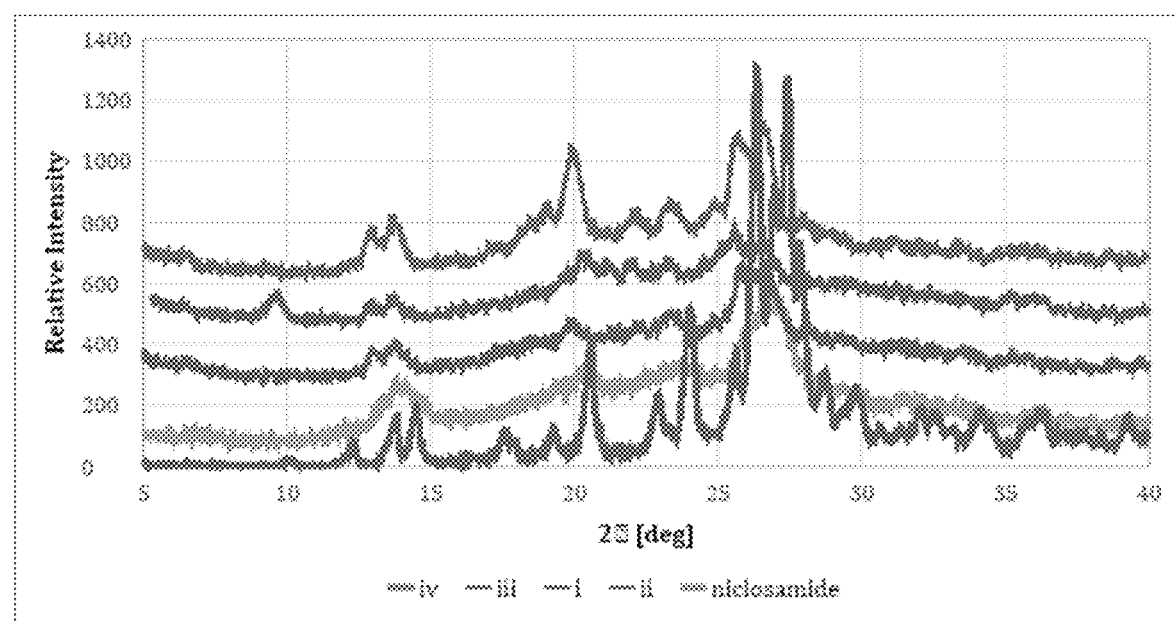

FIG. 15 shows the powder x-ray diffraction of crystalline niclosamide and four examples of niclosamide inhalation compositions.

Figure 16:
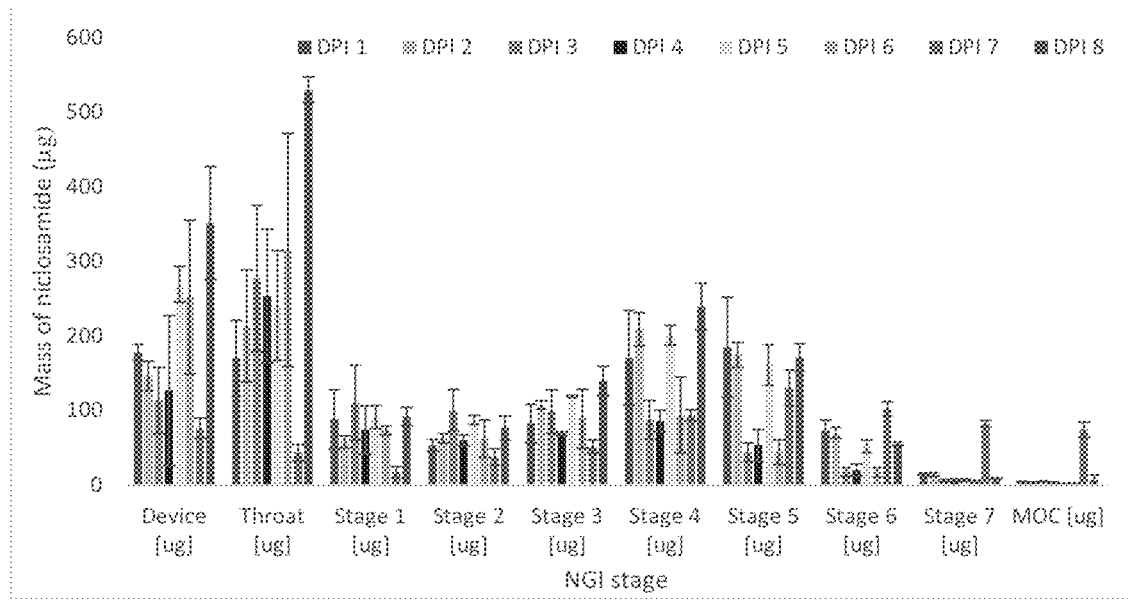

FIG. 16 shows the aerodynamic diameter distribution of DPIs 1-8.

Figure 17:
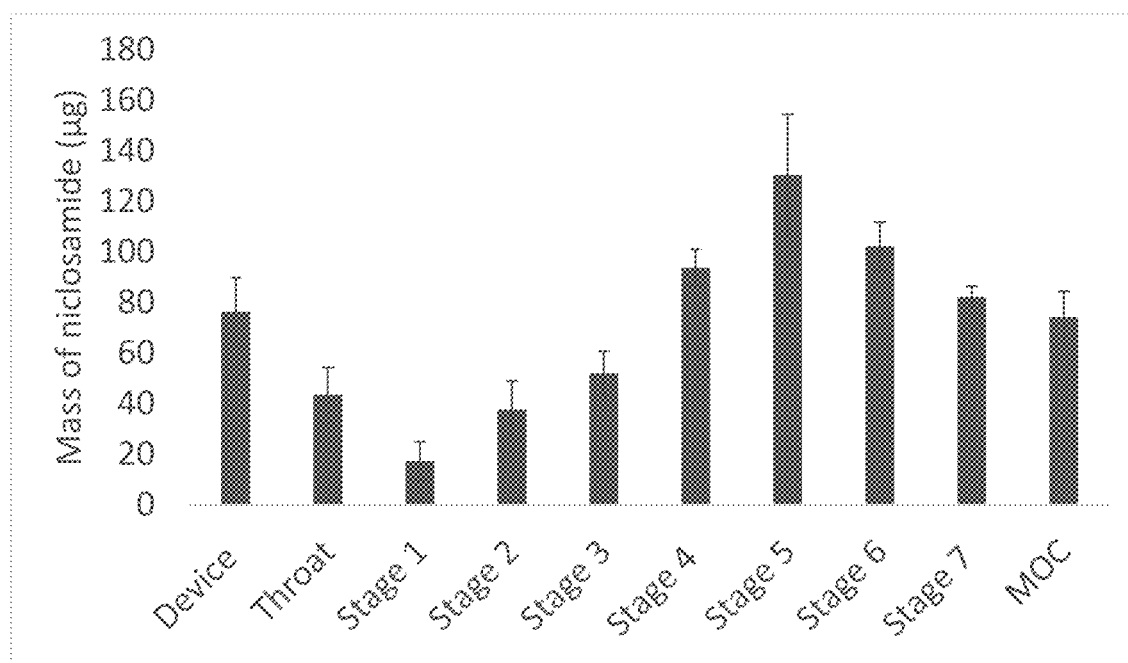

FIG. 17 shows the aerodynamic particle size distribution of niclosamide inhalation powder (n=3) made by thin-film freezing. The device bar indicates the remaining mass of niclosamide in the capsule and device. In the case of the throat bar, it indicates the remaining mass of niclosamide in the mouthpiece adapter and induction port.

Figure 18:
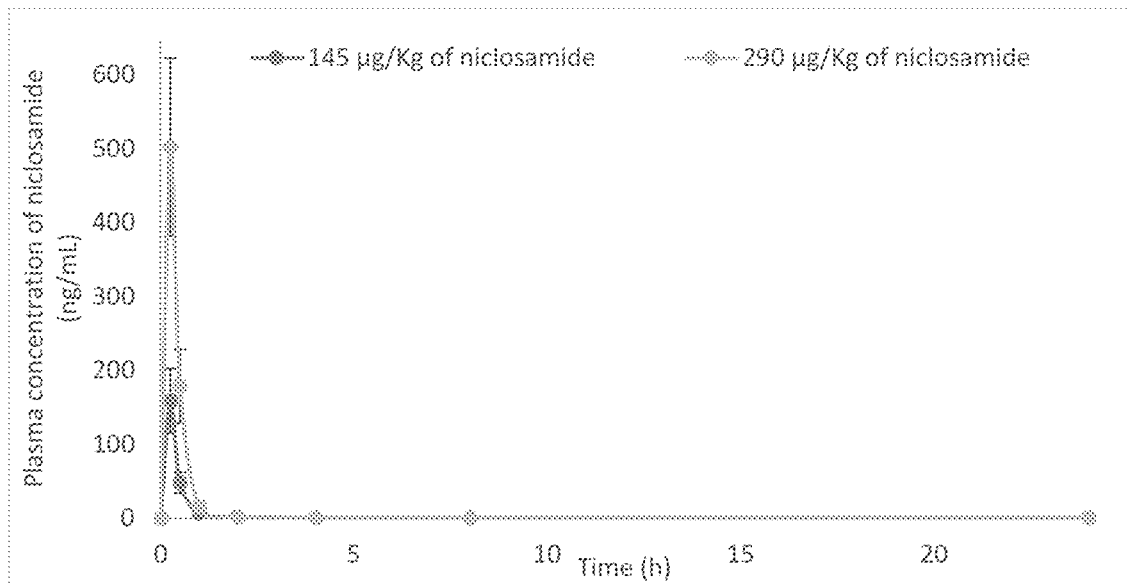

FIG. 18 shows the plasma concentration profile of niclosamide after the administration of niclosamide inhalation powder in Syrian hamsters (n=5 for each point). The groups received 8.7 (dark) and 17.4 (light) mg/Kg of niclosamide inhalation powder, containing a dose of 145 and 290 μg/Kg of niclosamide, respectively. The inset picture shows the profile within the first 2 h. Niclosamide $IC_{50}$ for SARS-CoV-2 is 0.28 μM (91.56 ng/mL) (Jeon et al., 2020).

Figure 19:
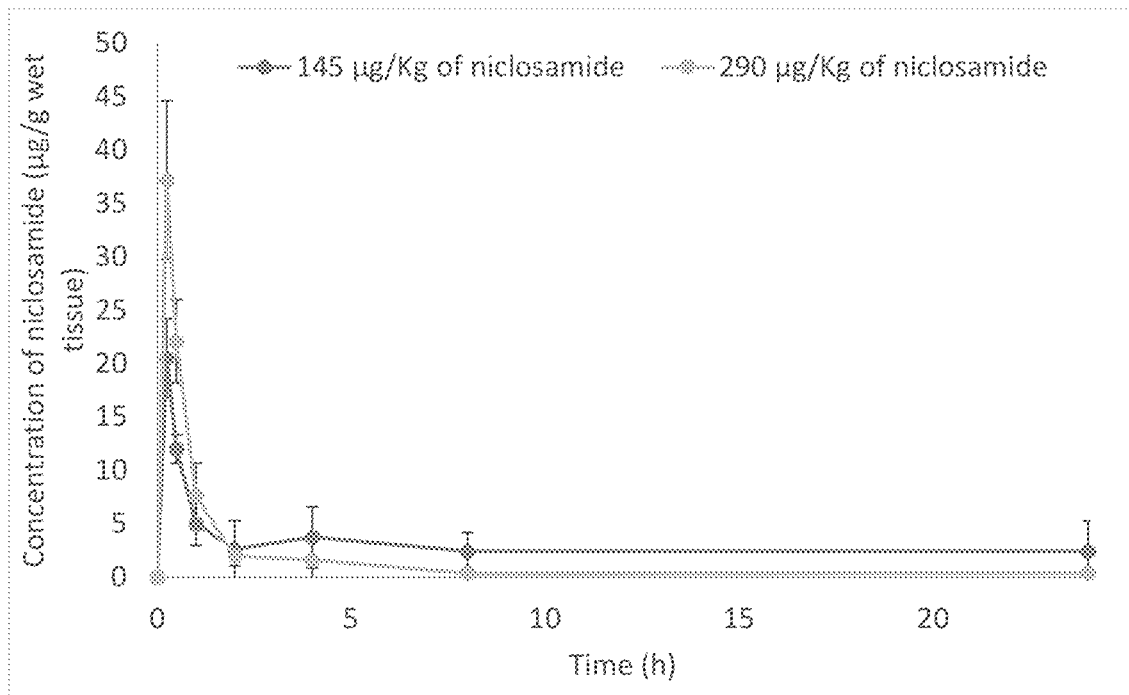

FIG. 19 shows lung concentration profile of niclosamide after the administration of niclosamide inhalation powder to Syrian golden hamsters (n=5). The groups received 8.7 (dark) and 17.4 (light) mg/Kg of niclosamide inhalation powder, containing a dose of 145 and 290 μg/Kg of niclosamide, respectively. The inset picture shows the profile within the first 2 h. Estimated niclosamide $IC_{50}$ for SARS-CoV-2 is 0.09156 μg/g of wet tissue, it was assumed that the wet tissue has a density of 1 g/m.

Figure 20:
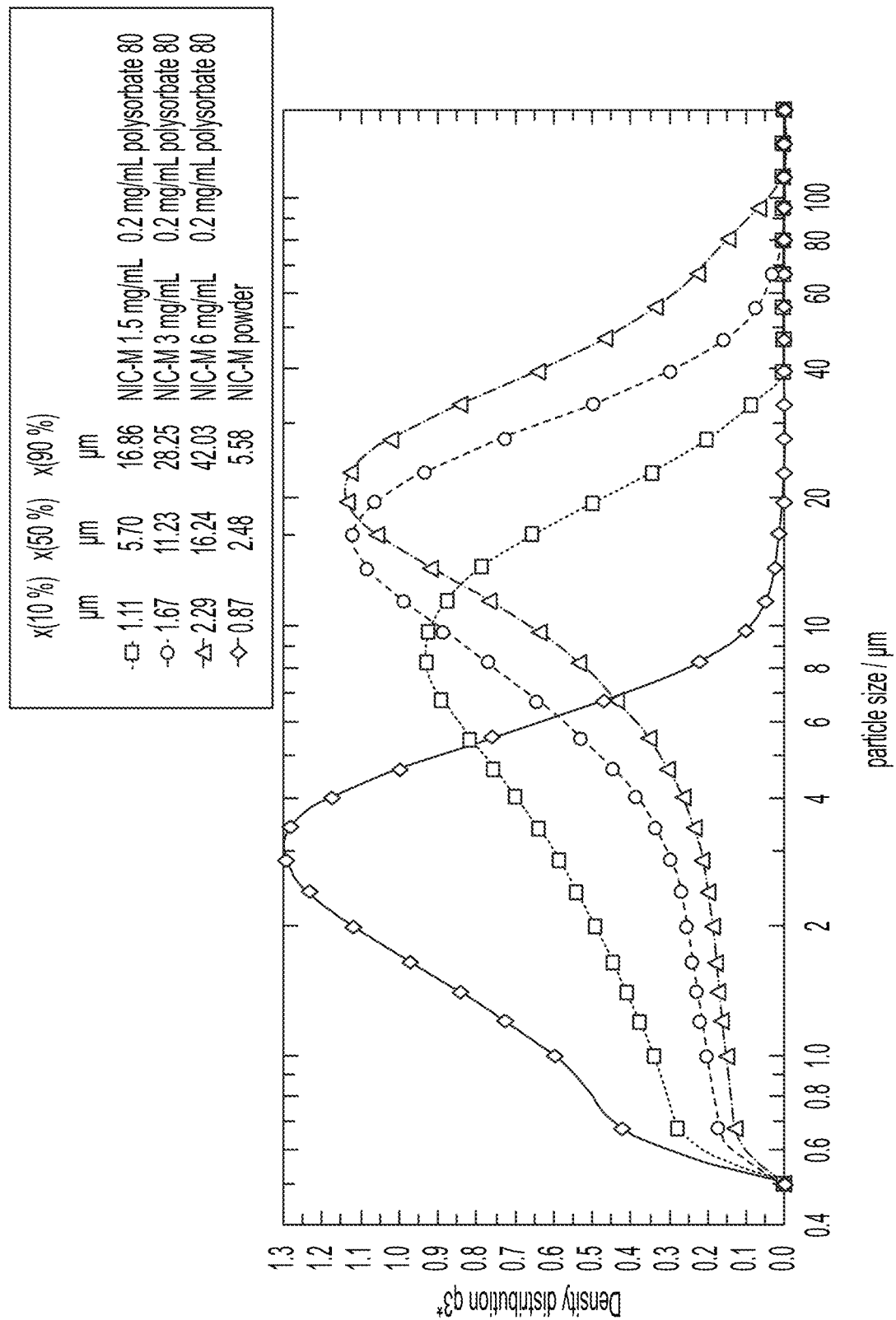

FIG. 20 shows the particle size distributions of micronized niclosamide suspensions prepared at varying concentrations, using polysorbate 80 0.2 mg/mL as a wetting and dispersing agent.

Figure 21:
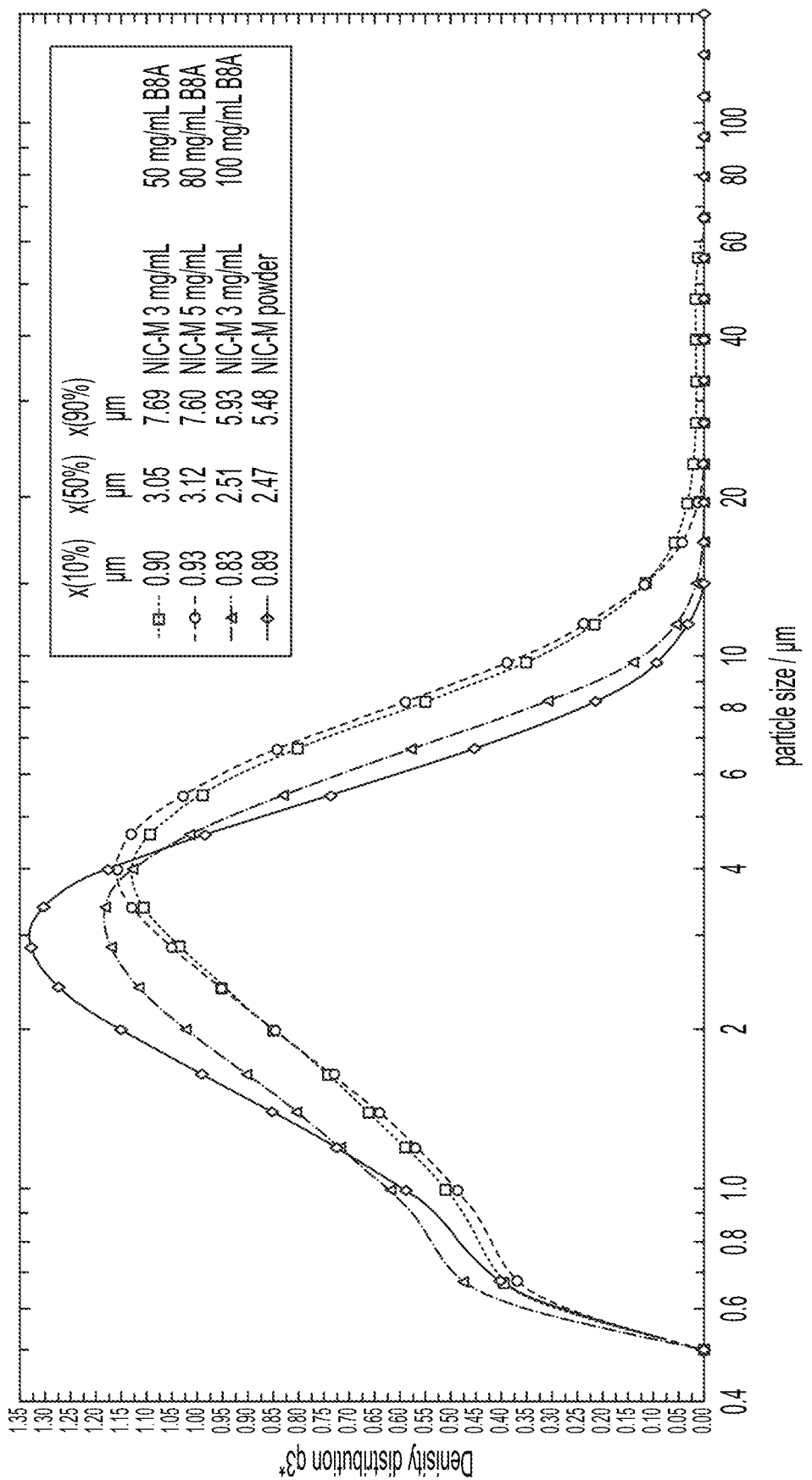

FIG. 21 shows the particle size distributions of micronized niclosamide suspensions prepared at varying concentrations, using bovine serum albumin (BSA) as a wetting and dispersing agent.

Figure 22:
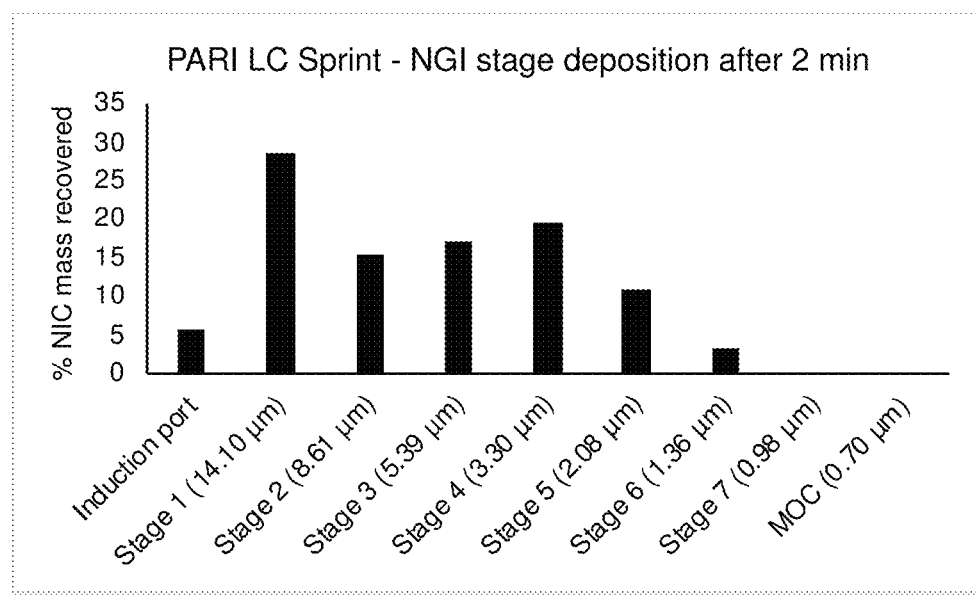

FIG. 22 shows the NGI stage deposition of NIC-M after 2 minutes of nebulization using the PARI® LC Sprint device.

Figure 23A:
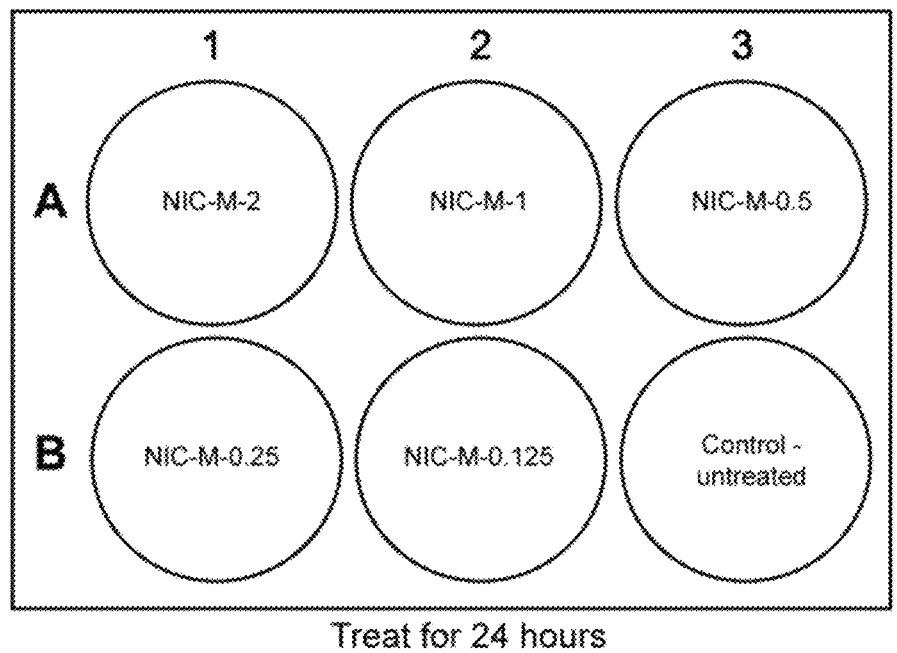
Figure 23B:
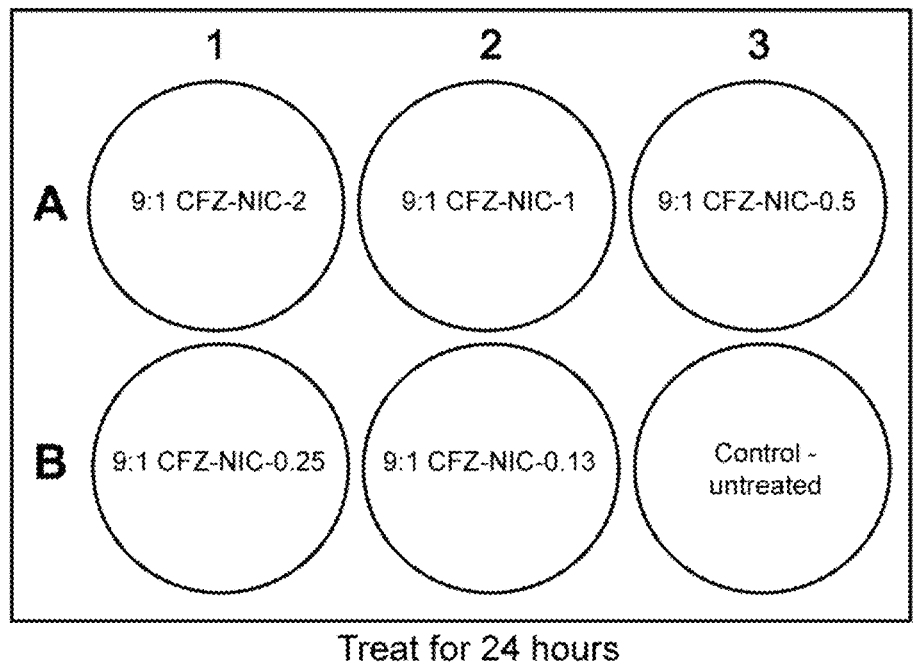
Figure 23C:
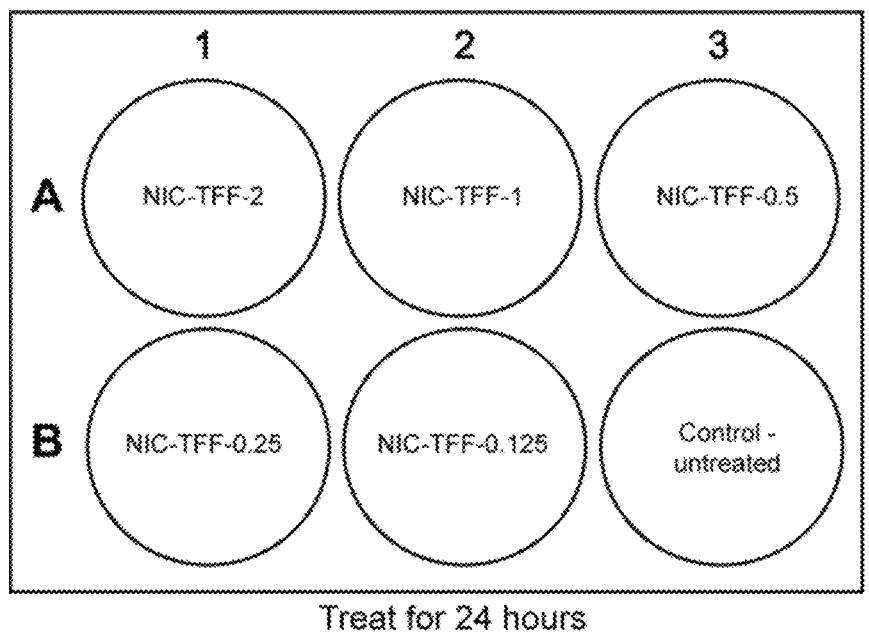

FIGS. 23A-23C shows the plate schematic for the SARS COV2 viral titer assays.

DESCRIPTION OF ILLUSTRATIVE EMBODIMENTS

In some aspects of the present disclosure, the pharmaceutical compositions provided herein may comprise niclosamide in formulations for administration for oral or inhalation. In some aspects, the present compositions may be used to deliver a therapeutically effective dose either to the lungs or to the gastrointestinal tract for systemic applications such as cancer. The present disclosure also provides methods of preparing these compositions or uses of these compositions to treat a disease or disorder such as a microbial infection or cancer.

Also provided herein are methods of preparing and using these compositions. Details of these compositions are provided in more detail below.

I. Pharmaceutical Compositions

In some aspects, the present disclosure provides pharmaceutical compositions containing an active agent, such as niclosamide, and may optionally contain an excipient. Theses composition may be formulated for administration orally or via inhalation.

A. Niclosamide

The pharmaceutical compositions described herein comprise niclosamide as an active agent. The pharmaceutical compositions described herein contain niclosamide in an amount between about 10% to about 90% w/w, between about 20% to about 80% w/w, between about 30% to about 70% w/w, or between about 40% to about 60% w/w of the total composition. In some embodiments, the amount of the niclosamide is from about 10%, 20%, 30%, 35%, 40%, 45%, 50%, 55%, 60%, 65%, 70%, 75%, 80%, to about 90% w/w or any range derivable therein.

In some aspects, a wide variety of different forms of niclosamide may be used. Niclosamide is an active agent with a chemical name of 5-Chloro-N-(2-chloro-4-nitrophenyl)salicylamide. The niclosamide used herein may be either anhydrous or may be a hydrate of niclosamide such as monohydrate of niclosamide. Furthermore, the niclosamide may be a salt such as an ethanolamine or piperazine salt. Additionally, co-crystal of niclosamide may be used in the pharmaceutical compositions may include co-crystals of niclosamide with 2-aminothiazole, benzamide, isoniazid, acetamide, caffeine, urea, p-aminobenzoic acid, theophylline, nicotinamide, or isonicotinamide (Sanphui et al., 2012; Luedeker et al., 2016). Alternative, it is also contemplated that known derivatives such as those described by Mook et al., 2015, which is incorporated herein by reference may also be used in the formulations. Additionally, niclosamide is light sensitive and should be stored in the dark to protect the composition from light.

1. Inhalation

In some embodiments, the present disclosure relates to respirable particles must be in the aerodynamic size range of around 0.5 to 5 microns or 0.5 to 3 microns in aerodynamic diameter. The mass median aerodynamic diameter of the pharmaceutical composition may be from about 0.4 μm, 0.5 μm, 0.6 μm, 0.8 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, to about 6.0 μm, or any range derivable therein. In some embodiments, the Copley® Inhaler Testing Data Analysis Software (CITDAS) version 3.10 (Copley Scientific, Nottingham, UK) is used to calculate the aerodynamic particle size distribution including mass median aerodynamic diameter (MMAD), fine particle fraction (FPF), geometric standard deviation (GSD) and emitted fraction (EF). Mass median aerodynamic (MMAD) and geometric standard deviation (GSD) were evaluated by the cumulative percentage of mass and the aerodynamic diameter. Typical approaches to obtain particles of this size range is by air jet milling, spray drying, thin-film freezing, and other methods known in the art. Regardless of the method used to achieve drug particles in the appropriate size range, micronization results in highly cohesive particles that are generally resistant to aerosol dispersion. This is typically overcome through formulation as interactive mixtures with larger lactose carrier particles (e.g., 45-75 μm) or other dispersion enhancing excipients. Drug particles are admixed by blending with appropriate carrier(s) particles using conventional mixing, or the drug and carrier can be prepared simultaneously from a solution or suspension formulation such as by spray-drying or thin film freezing processes.

In some aspects, the present disclosure provides the excipient free niclosamide powder via oral inhalation in a dual delivery mode that exhibits limited dissolution increasing local accumulation and that is readily phagocytized by macrophages. Approximately 30-60% of the delivered dose is administered to the lung tissues which is necessary to directly and rapidly treat infections in the lung. In addition, 40-70% of the delivered dose is administered to the oral cavity (mouth and throat) which is then swallowed. As an infection may further reside in the gastrointestinal tract, the orally inhaled dose is also delivered in significant amounts to the gastrointestinal tract. The excipient free nature of the orally inhaled powder ensures that adequate doses are delivered to both lung and gastrointestinal target sites. Thirdly, since the D10 (small particle fraction) is relatively small with a significant proportion of particles being in the diffusive sub-micron size range, a patient exhaling through the nasal cavity will also have appreciable deposition in the nasal mucosa where some infection may be present.

Some embodiments of the pharmaceutical compositions described herein the particles contain the niclosamide and the excipients in a single particle. Furthermore, these pharmaceutical compositions may contain one or more properties that allow them to be delivered to the lungs through an inhaler. These pharmaceutical compositions show enhanced ability to break into smaller components. The pharmaceutical compositions may show a high surface area, a low tapped density, or a low bulk density. The surface area of the pharmaceutical compositions may be greater than 10 $m^2/g$, greater than 25 $m^2/g$, or greater than 50 $m^2/g$. The bulk density of the pharmaceutical compositions may be less than 1 g/mL, less than 0.5 g/mL, or less than 0.25 g/mL. Finally, the tapped density of the pharmaceutical compositions may be less than 0.1 $g/cm^3$, 0.05 $g/cm^3$, or 0.025 $g/cm^3$. Furthermore, these compositions may show improved flowability or compressibility such as a low Carr's Index such as less than 20, less than 15, or less than 10.

In some embodiments, the present disclosure provides methods for the administration of the inhalable niclosamide composition provided herein using a device. Administration may be, but is not limited, to inhalation of niclosamide using an inhaler. In some embodiments, an inhaler is a simple passive dry powder inhaler (DPI), such as a Plastiape RSO1 monodose DPI. In a simple dry powder inhaler, dry powder is stored in a capsule or reservoir and is delivered to the lungs by inhalation without the use of propellants.

In some embodiments, an inhaler is a single-dose DPI, such as a DoseOne™, Spinhaler, Rotohaler®, Aerolizer®, or Handihaler. In some embodiments, an inhaler is a multidose DPI, such as a Plastiape RS02, Turbuhaler®, Twisthaler™, Diskhaler®, Diskus®, or Ellipta™. In some embodiments, the inhaler is Twincer®, Orbital®, TwinCaps®, Powdair, Cipla Rotahaler, DP Haler, Revolizer, Multi-haler, Twister, Starhaler, or Flexhaler®. In some embodiments, an inhaler is a plurimonodose DPI for the concurrent delivery of single doses of multiple medications, such as a Plastiape RSO4 plurimonodose DPI. Dry powder inhalers have medication stored in an internal reservoir, and medication is delivered by inhalation with or without the use of propellants. Dry powder inhalers may require an inspiratory flow rate greater than 30 L/min for effective delivery, such as between about 30-120 L/min.

In some embodiments, the inhalable niclosamide is delivered as a propellant formulation, such as HFA propellants.

In some embodiments, the inhaler may be a metered dose inhaler. Metered dose inhalers deliver a defined amount of medication to the lungs in a short burst of aerosolized medicine aided by the use of propellants. Metered dose inhalers comprise three major parts: a canister, a metering valve, and an actuator. The medication formulation, including propellants and any required excipients, are stored in the canister. The metering valve allows a defined quantity of the medication formulation to be dispensed. The actuator of the metered dose inhaler, or mouthpiece, contains the mating discharge nozzle and typically includes a dust cap to prevent contamination.

In some embodiments, an inhaler is a nebulizer. A nebulizer is used to deliver medication in the form of an aerosolized mist inhaled into the lungs. The medication formulation be aerosolized by compressed gas, or by ultrasonic waves. A jet nebulizer is connected to a compressor. The compressor emits compressed gas through a liquid medication formulation at a high velocity, causing the medication formulation to aerosolize. Aerosolized medication is then inhaled by the patient. An ultrasonic wave nebulizer generates a high frequency ultrasonic wave, causing the vibration of an internal element in contact with a liquid reservoir of the medication formulation, which causes the medication formulation to aerosolize. Aerosolized medication is then inhaled by the patient. A nebulizer may utilize a flow rate of between about 3-12 L/min, such as about 6 L/min. In some embodiments, the nebulizer is a dry powder nebulizer.

In some embodiments, the composition may be administered on a routine schedule. As used herein, a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In some embodiments, niclosamide is administered once per day. In preferred embodiments, niclosamide is administered less than once per day, such as every other day, every third day, or once per week. In some embodiments, a complete dose of niclosamide is between 0.05-30 mg, such as 0.1-10, 0.25-5, 0.3-5, or 0.5-5 mg.

In some embodiments, niclosamide may be provided in a unit dosage form, such as in a capsule, blister or a cartridge, wherein the unit dose comprises at least 0.25 mg of niclosamide, such as at least 0.5 mg or 1 mg of niclosamide per dose. In particular aspects, the unit dosage form does not comprise the administration or addition of any excipient and is merely used to hold the powder for inhalation (i.e., the capsule, blister, or cartridge is not administered). In some embodiments, niclosamide may be administered in a high emitted dose, such as at least 1 mg, preferably at least 10 mg, even more preferably 50 mg. In some embodiments, administration of micronized niclosamide results in a high fine particle dose into the deep lung such as greater than 1 mg. Preferably, the fine particle dose into the deep lung is at least 5 mg, even more preferably at least 10 mg.

In some embodiments, changes in pressure drop across the device result in a change in emitted dose. In some embodiments, changes in pressure drop across the device of 3 kPa, such as from 4 kPa to 1 kPa, result in a reduction of emitted dose of less than 35%, such as 34%, 33%, 32%, 31%, 30%, 29%, 28%, 27%, 26%, 25%, 24%, 23%, 22%, 21%, 20%, 19%, 18%, 17%, 16%, 15% or less. In some embodiments, changes in inhalation pressure drop across the device result in a change in fine particle dose. In some embodiments, changes in inhalation pressure drop across the device of 3 kPa, such as from 4 kPa to 1 kPa result in a reduction of fine particle dose of less than 35%, such as 34%, 33%, 32%, 31%, 30%, 29%, 28%, 27%, 26%, 25%, 24%, 23%, 22%, 21%, 20%, 19%, 18%, 17%, 16%, 15% or less.

2. Oral

Niclosamide is a poorly water soluble, lipophilic molecule previously known to have poor and variable bioavailability which for its current approved indication for treating helminthic infections in the gastrointestinal tract is not a limiting factor. When attempting to repurpose the medication for the treatment of diseases such as prostate cancer which require systemic concentrations of the drug, the challenges to overcome the bioavailability limitations become clear. As niclosamide is both poorly water soluble and lipophilic, the rate limiting step for the oral absorption of the drug is the dissolution of the molecule.

Unfortunately, the majority of drugs that show pharmacological activity against cancers in vitro are poorly water-soluble and thus exhibit poor or no bioavailability. While often not a limitation for their currently approved indications, their usefulness in treating cancers often requires significantly better absorption of the drugs to achieve drug concentrations sufficient for tumor inhibition.

Amorphous solid dispersions are used to improve the solubility and bioavailability of poorly water-soluble drugs. They are used to overcome limitations of solubility by the pharmaceutical industry in 19 commercial products approved by the Food & Drug Administration between 2007 and 2017. Most often these products are based on binary mixtures of the drug and a hydrophilic polymer. However, these formulations can be limited for drugs with specific physicochemical properties and dose requirements, such as highly lipophilic drugs like atovaquone (Friesen et al., 2008).

In some embodiments, the composition may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In some embodiments, niclosamide is administered once per day. In preferred embodiments, miclosamide is administered less than once per day, such as every other day, every third day, or once per week. In some embodiments, a complete dose of niclosamide is between from about 100 mg to about 5 g, such as 100 mg, 200 mg, 300 mg, 400 mg, 500 mg, 600 mg, 700 mg, 800 mg, 900 mg, 1 g, 1.25 g, 1.5 g, 1.75 g, 2 g, 2.5 g, 3 g, 3.5 g, 4 g, 4.5 g, to about 5 g, or any range derivable therein.

3. Uses of Compositions

Several clinical indications would benefit from administration of niclosamide compositions with enhanced bioavailability. These indications include the infections of a microorganism such as bacteria, a virus, a parasite, or a worm. In particular, the compositions may be used to treat a viral infection. Some non-limiting examples of viral infections which may be treated with the composition described herein include COVID-10, MERS, SARS, influenza, Zika, Lassa, Ebola, HIV including HIV with complications such as TB, and adenovirus. In other embodiments, the pharmaceutical compositions may be used to treat schistosomiasis and related pulmonary complications. Additionally, these pharmaceutical compositions may be used to treat vancomycin resistant enterococci, *Pseudomonas aeruginosa, Acinetobacter baumannii, Klebsiella pneumoniae, C. difficile*, or MRSA. Furthermore, the pharmaceutical composition may be used to treat or control diabetes. With regards to viral infections, some viruses such as SARS-CoV can enter cells and replicate where ACE2+ tissues are present, which includes areas such as the kidneys, lungs and small intestine (Hoffmann et al., 2020). Other such clinical indications include several cancers, in particular castration-resistant prostate cancer, glioblastoma, or lung cancer.

Although for many men prostate cancer, the most commonly diagnosed cancer in men, is treatable, there continues to be nearly 30,000 deaths from the disease each year (Bray et al., 2018). Prostate cancer is currently treated by inhibiting the androgen receptor (AR) signaling program, in some cases requiring castration to treat the disease. However, in some instances the cancer is resistant to castration making it difficult to successfully treat. Recently, it has been discovered that even in castration-resistant prostate cancer the AR signaling plays an important role and is characterized by changes in the AR, which despite castrate levels of androgen continue to result in the transcription of target genes and tumor progression (Liu et al., 2016) This has led to the development of a next generation of AR signaling inhibitor drugs (i.e., enzalutamide and abiraterone) that have shown improvements in the overall survival of these patients (Matsubara et al., 2018). Unfortunately for these patients, resistance to the next generation AR signaling inhibitors is inevitable and occurs within the first one to two years after initiating therapy (Kim and Ryan, 2012). The resistance to these agents has been recently shown to be linked with AR variants. Alternative mRNA splicing generates AR variants which are up-regulated in castration-resistant prostate cancer patients and are associated with prostate cancer progression and resistance to AR-targeted therapy (Mostaghel et al., 2018; Li et al., 2013; Zhang et al., 2011). In particular, variant AR-V7 has been shown to be upregulated in enzalutamide resistant prostate cancer cells (Liu et al., 2014). Targeting AR variants, specifically AR-V7 (Liu et al., 2014), has the potential to overcome resistance to this next generation of AR drugs and improve treatment of advanced prostate cancer.

In a recent study, a library of 1120 μmall molecules and approved drugs was used to discover a compound that inhibits AR-V7 expression using a high throughput screening technique for AR-V7 activity (Liu et al., 2014). Niclosamide, a drug FDA approved for the treatment of human tapeworm infections was identified. Niclosamide was shown to overcome resistance to enzalutamide in enzalutamide resistant prostate cancer cell lines in vitro as well as in vivo when niclosamide was dosed by intraperitoneal injection. Niclosamide has been previously explored for the treatment of other cancers such as colorectal cancer based on its multi-targeted mechanism of action, inhibiting the Wnt/β-catenin pathway, mammalian target of rapamycin complex 1 (mTORC1), the signal transducers and activators of transcription 3 (STAT3) pathway, the nuclear factor-kappaB (NF-κB) and the Notch signaling pathway (Li et al., 2014. The mechanism in which niclosamide suppresses cell migration and invasion of enzalutamide resistant prostate cancer cells is via inhibition of the STAT3-AR axis (Liu et al., 2015). In addition to overcoming enzalutamide resistance, niclosamide has also been shown to enhance abiraterone treatment in castration-resistant prostate cancer cells in vitro and in vivo with oral niclosamide treatment, although at a dose of 500 mg/kg, known to exceed the maximum oral tolerated dose in humans (Schweizer et al., 2018; Liu et al., 2016).

Based on the promising evidence from several studies showing the effect of niclosamide on castration-resistant prostate cancer, a phase I study testing the safety, tolerability and pharmacokinetics of the known to be poorly absorbed niclosamide was performed in castration-resistant patients. At doses exceeding those currently used for treating helminthic infections in an attempt to achieve sufficient niclosamide concentrations for cancer activity the investigators concluded "the development of the current oral formulation of niclosamide as a cancer therapy should not be pursued. Attention must be turned to developing niclosamide analogs with improved oral bioavailability" (Schweizer et al., 2018). Based on the promising data in vitro and presented in mouse models together with the poor performance shown in the phase I clinical trial as a result of the poor pharmacokinetic profile of niclosamide in its current formulation, overcoming the bioavailability limitations for niclosamide with an improved formulation has the potential to enable niclosamide to be an effective therapeutic for the treatment of advanced prostate cancer.

In some embodiments, the pharmaceutical composition may be used to treat one or more diseases or disorders in combination with one or more additional active agents. In particular, the pharmaceutical composition may be used in conjunction with another antimicrobial agent or active agent which reduces one or more symptoms of the microbial infection. Some non-limiting examples of additional therapeutic agents may include chloroquine, hydroxychloroquine, thalidomide, plasminogen, colistin, polymyxin B, or clofazimine. In other compositions, the pharmaceutical composition may be used in conjunction with one or more anti-cancer agents such as a chemotherapeutic agent, radiotherapy, surgery, or immunotherapy. Some non-limiting examples of additional therapeutic agents may include abiraterone such as abiraterone acetate, enzalutamide, or bicalutamide.

B. Excipients

In some aspects, the present disclosure comprises one or more excipients formulated into pharmaceutical compositions. An "excipient" refers to pharmaceutically acceptable carriers that are relatively inert substances used to facilitate administration or delivery of an API into a subject or used to facilitate processing of an API into drug formulations that can be used pharmaceutically for delivery to the site of action in a subject. Non-limiting examples of excipients include stabilizing agents, surfactants, surface modifiers, solubility enhancers, buffers, encapsulating agents, antioxidants, preservatives, nonionic wetting or clarifying agents, viscosity increasing agents, and absorption-enhancing agents. Additionally, cyclodextrin compounds such a sulfo ethyl β cyclodextrin may be used as excipients. Furthermore, one or more flow enhancing agents such as magnesium salts may be used. Some non-limiting examples of flow enhancing agents include magnesium stearate, sodium stearyl fumarate, and L-leucine.

In some embodiments, the amount of the excipient in the pharmaceutical composition is from about 25% w/w to about 95% w/w, from about 40% w/w to about 90% w/w, or from about 60% w/w to about 85% w/w. In some embodiments, the amount of the excipient in the pharmaceutical composition is from about 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, to about 95% w/w, or any range derivable therein. In some aspects, the amount of a further excipient in the pharmaceutical composition is from about 0.1% to about 25% w/w, from about 0.25% to about 20% w/w, from about 0.25% to about 5% w/w, or from about 5% to about 20% w/w. The amount of the excipient in the pharmaceutical composition comprises from about 0.1%, 0.25%, 0.5%, 1%, 1.5%, 2%, 2.5%, 3%, 3.5%, 4%, 4.5%, 5%, 5.5%, 6%, 6.5%, 7%, 7.5%, 8%, 9%, 10%, 12%, 14%, 16%, 18%, 20%, 22%, 24%, to about 25% w/w, or any range derivable therein, of the total pharmaceutical composition.

In some aspects, the present disclosure may further comprise one or more excipient such as a saccharide, a pharmaceutically acceptable polymer, or a surfactant. Some composition may further comprise a mixture of two or more excipients including two or more surfactants.

1. Saccharides

In some aspects, the present disclosure comprises one or more excipients formulated into pharmaceutical compositions. In some embodiments, the excipients used herein are water soluble excipients. These water-soluble excipients include carbohydrates or saccharides such as disaccharides such as sucrose, trehalose, or lactose, a trisaccharide such as fructose, glucose, galactose comprising raffinose, polysaccharides such as starches or cellulose, or a sugar alcohol such as xylitol, sorbitol, or mannitol. In some embodiments, these excipients are solid at room temperature. Some non-limiting examples of sugar alcohols include erythritol, threitol, arabitol, xylitol, ribitol, mannitol, sorbitol, galactitol, fucitol, iditol, inositol, volemitol, isomalt, maltitol, lactitol, maltotritol, maltotetraitol, or a polyglycitol. In other aspects, larger molecules like amino acids, peptides and proteins are incorporated to facilitate inhalation delivery, including leucin, trileucine, histidine and others.

2. Pharmaceutically Acceptable Polymers

In some aspects, the present disclosure provides compositions which may further comprise a pharmaceutically acceptable polymer. In some embodiments, the polymer has been approved for use in a pharmaceutical formulation and is known to undergo softening or increased pliability when raised above a specific temperature without substantially degrading.

When a pharmaceutically acceptable polymer is present in the composition, the pharmaceutically acceptable polymer is present in the composition at a level between 1% to 90% w/w, between 10% to 80% w/w, between 20% to 70% w/w, between 30% to 70% w/w, between 40% to 60% w/w. In some embodiments, the amount of the pharmaceutically acceptable thermoplastic polymer is from about 5%, 10%, 15%, 50%, 20%, 25%, 30%, 35%, 37.5%, 40%, 41%, 42%, 43%, 44%, 45%, 46%, 47%, 48%, 49%, 50%, 51%, 52%, 53%, 54%, 55%, 56%, 57%, 58%, 59%, 60%, 65%, 70%, 80%, to about 90% w/w or any range derivable therein.

Within the compositions described herein, a single polymer or a combination of multiple polymers may be used. In some embodiments, the polymers used herein may fall within two classes: cellulosic and non-cellulosic. These classes may be further defined by their respective charge into neutral and ionizable. Ionizable polymers have been functionalized with one or more groups which are charged at a physiologically relevant pH. Some non-limiting examples of neutral non-cellulosic polymers include polyvinyl pyrrolidone, polyvinyl alcohol, copovidone, and poloxamer. Within this class, in some embodiments, pyrrolidone containing polymers are particularly useful. Some non-limiting examples of ionizable cellulosic polymers include cellulose acetate phthalate and hydroxypropyl methyl cellulose acetate succinate. Finally, some non-limiting examples of neutral cellulosic polymers include hydroxypropyl cellulose, hydroxypropyl methyl cellulose, hydroxyethyl cellulose, and hydroxymethyl cellulose.

Some specific pharmaceutically acceptable polymers which may be used include, for example, Eudragit™ RS PO, Eudragit™ S100, Kollidon SR (poly(vinyl acetate)-co-poly (vinylpyrrolidone) copolymer), Ethocel™ (ethylcellulose), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), carboxymethyl cellulose and alkali metal salts thereof, such as sodium salts sodium carboxymethyl-cellulose (CMC), dimethylaminoethyl methacrylate-methacrylic acid ester copolymer, carboxymethylethyl cellulose, carboxymethyl cellulose butyrate, carboxymethyl cellulose propionate, carboxymethyl cellulose acetate butyrate, carboxymethyl cellulose acetate propionateethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly (methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, poly(methacylic acid-co-methyl methacrylate 1:2), poly(methacrylic acid-co-methyl methacrylate 1:1), Poly(methyl acrylate-co-methyl methacrylate-co-methacrylic acid 7:3:1), poly(butyl methacrylate-co-(2-dimethylaminoethyl) methacrylate-co-methyl methacrylate 1:2:1), poly(ethyl acrylate-co-methyl methacrylate 2:1), poly(ethyl acrylate-co-methyl methacrylate 2:1), poly(ethyl acrylate-co-methyl methacrylate-co-trimethylammonioethyl methacrylate chloride 1:2:0.2), poly(ethyl acrylate-co-methyl methacrylate-co-trimethylammonioethyl methacrylate chloride 1:2:0.1), Eudragit L-30-D™ (MA-EA, 1:1), Eudragit L-100-55™ (MA-EA, 1:1), hydroxypropylmethylcellulose acetate succinate (HPMCAS), polyvinyl caprolactam-polyvinyl acetate-PEG graft copolymer, polyvinyl alcohol/acrylic acid/methyl methacrylate copolymer, polyalkylene oxide, Coateric™ (PVAP), Aquateric™ (CAP), and AQUACOAT™ (HPMCAS), polycaprolactone, starches, pectins, chitosan or chitin and copolymers and mixtures thereof, and polysaccharides such as tragacanth, gum arabic, guar gum, and xanthan gum.

In some embodiments, the compositions described herein contain a pharmaceutically acceptable polymer selected from povidone, copovidone, polyvinyl pyrrolidone, polyvinyl acetate, and SOLUPLUS® (polyvinyl caprolactampoly-vinyl acetate-polyethylene glycol graft co-polymer, commercially available from BASF). In particular, the pharmaceutical acceptable polymer may be a copolymer of polyvinyl pyrrolidone and polyvinyl acetate. In particular, the copolymer may comprises about 5-7 vinyl pyrrolidone units to about 3-5 units of vinyl acetate, in particular 6 units of vinyl pyrrolidone and 4 units of vinyl acetate. The number-average of the molecular weight of the polymer may be from about 15,000 to about 20,000. The pharmaceutically acceptable polymer may be Kollidan® VA 64 (copovidone, vinylpyrrolidone-vinyl acetate) having a CAS Number of 25086-89-9.

3. Surfactants

In some embodiments, the present disclosure comprises one or more surfactants. The surfactant may be a fatty acid, a triglyceride, an ester of a fatty acid, or mixtures thereof. The term lipid includes fatty acids which are a group of aliphatic saturated or unsaturated carboxylic acids. The chains are usually unbranched and have 6 to 30, preferably 8 to 22. and in particular 8 to 18, carbon atoms. Some non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid. Additionally, the term includes unsaturated fatty acids may be unsaturated one or more times, in particular unsaturated once, twice, three times, four times, five times or six times. Some non-limiting examples of singly unsaturated fatty acids include palmitoleic acid, oleic acid and erucic acid, of doubly unsaturated fatty acids include sorbic acid and linoleic acid, of triply unsaturated fatty acids include linolenic acid and eleostearic acid, of quadruply unsaturated fatty acids include arachidonic acid, of quintuply unsaturated fatty acids include clupanodonic acid, and of sextuply unsaturated fatty acids include docosahexaenoic acid.

Alternatively, the surfactants may include glycerides which are esters of glycerol. Depending on the number of ester groups, the glyceride may be referred to as a mono-, di- and triglycerides. The acid residue in a monoglyceride may be at position 1 or 2 and the acid residues of di- and triglycerides may be identical or different and be distributed in every conceivable way over the three possible positions of glycerol. The acid residues are preferably the fatty acids described above. Examples of monoglycerides include glycerol monobehenate, glycerol monocaprate, glycerol monococoate, glycerol monoerucate, glycerol monoisostearate, glycerol monolinoleate, glycerol monolaurate, glycerol monolinoleate, glycerol monomyristate, glycerol monooleate, glycerol monopalmitate, glycerol monoricinoleate, glycerol monostearate, of the diglycerides include glycerol dicaprylate, glycerol dilaurate, glycerol dimyristate, glycerol dioleate, glycerol dipalmitate and glycerol distearate, of the triglycerides include glycerol tricaprylate, glycerol trilaurate, glycerol trimyristate, glycerol trioctanoate, glycerol trioleate, glycerol triricinoleate and glycerol tristearate. Many common pharmaceutical surfactants comprises one or more glycerides and these pharmaceutical surfactants include Capmul® (a group of monoglycerides or diglycerides), CapTex® (decanoic acid; octanoic acid: propane-1,2,3-triol), and Labrafil® (2-[2,3-bis(2-hydroxyethoxy)propoxy]ethanol; hexadecanoic acid; octadecanoic acid). Additionally, other surfactants may include esters of fatty acids such as methyl palmitate, ethyl linoleate, or isopropyl palmitate.

As used herein, the term surfactant refers to a compound which exhibits amphiphilic character and reduces the surface tension of a solvent, particularly water. Surfactants can generally be classified into four categories: cationic, anionic, zwitterionic, or non-ionic. While it is contemplated that any of these surfactants may be used in the present compositions, non-ionic surfactant shows particular promise. Cationic surfactants include, but are not limited to, amines with long alkyl chains and are protonated at a physiologically relevant pH or permanently charged quaternary ammonium salts such as cetrimonium bromide, cetylpyridinium chloride, benzalkonium chloride, benzethonium chloride, dimethyldioctadecylammonium chloride, or dioctadecyldimethylammonium bromide. Some non-limiting examples of anionic surfactants include sulfate, sulfonate, or phosphate esters such as docusate, perfluorooctanesulfonate, perfluorobutanesulfonate, alkyl-aryl ether phosphates, or alkyl ether phosphate or carboxylate esters including alipathic carboxylates such as fatty acids and derivatives thereof. Other examples of zwitterionic surfactants including phospholipids such as phosphotidylserine, phosphotidylcholine, phosphotidylethanolamine, or sphingomyelins, sultaines such as CHAPS (3-[(3-Cholamidopropyl)dimethylammonio]-1-propanesulfonate) and cocamidopropyl hydroxysultaine, or betaine such as cocamidopropyl betaine. Finally, some non-limiting examples of nonionic surfactants include PEG alkyl ethers, polypropylene glycol ethers, glucoside alkyl ethers, PEG alkylaryl ethers such as Triton® (2-[4-(2,4,4-trimethylpentan-2-yl)phenoxy]ethanol) and nonoxynol, simple alkyl esters of glycerol such as glycerol laurate, polysorbates such as Tween® (polyethylene glycol sorbitan monolaurate), Sorbitan alkyl esters such as Span, or Poloxamer® (triblock copolymers of polyethylene glycol and polypropylene glycol) and other block copolymers of polyethylene glycol and polypropylene glycol. In some embodiments, the surfactants used in the present pharmaceutical compositions contain one or more polyethylene glycol or polypropylene glycol polymer such as Tween® (polyethylene glycol sorbitan monolaurate), Capryol® (propylene glycol monocaprylate), Labrafil® (2-[2,3-bis(2-hydroxyethoxy)propoxy]ethanol; hexadecanoic acid; octadecanoic acid), or Labrasol® (caprylocaproyl macrogol-8 glycerides, caprylocaproyl polyoxyl-8 glycerides, polyoxylglycerides).

In some aspects, the present disclosure provides a surfactant which includes a PEG polymer with a molecular weight from about 100 to about 4000 daltons, from about 100 to about 1000 daltons, from about 100 to about 500 daltons, or from about 100, 200, 300, 400, 500, 600, 700, 800, 900, 1000, 1250, 1500, 1750, 2000, 2500, 3000, 3500, or about 4000 daltons. In some embodiments, the PEG polymer further comprises a hydrophobic group such as a vitamin or fatty acid. In some embodiments, the hydrophobic group may be a vitamin such as vitamin E. Such a compound may further comprise a linking group such as a diamine or dicarboxylic acid such as 1,2-ethylenediamine or succinic acid. The surfactant group may be a PEGylated tocopherol succinate such as TPGS 1000 or similar tocopherol succinate compounds.

In some aspects, the amount of the total surfactant is from about 1% to about 20% w/w, from about 2% to about 10% w/w, from about 2% to about 8% w/w, or from about 4% to about 6% w/w. The amount of total surfactant comprises from about 1%, 1.25%, 1.5%, 1.75%, 2%, 3%, 4%, 5%, 6%, 7%, 8%, 9%, 10%, 12%, 14%, 15%, 16%, 18%, to about 20% w/w, or any range derivable therein, of the total pharmaceutical composition. In one embodiment, the amount of each surfactant is at 0.5% to 10% w/w of the total weight of the pharmaceutical composition. The amount of each surfactant comprises from about 0.25%, 0.5%, 0.75%, 1%, 1.25%, 1.5%, 1.75%, 2%, 2.25%, 2.5%, 2.75%, 3%, 4%, 5%, 6%, 7%, 8%, 9%, to about 10% w/w, or any range derivable therein, of the total pharmaceutical composition.

II. Manufacturing Methods

A. Hot Melt Extrusion

Thus, in one aspect, the present disclosure provides pharmaceutical compositions which may be prepared using a thermal or fusion-based high energy process. Such process may include hot melt extrusion, hot melt granulation, melt mixing, spray congealing, sintering/curing, injection molding, or a thermokinetic mixing process such as the KinetiSol method. Similar thermal processing methods are described in LaFountaine et al., 2016a, Keen et al., 2013, Vynckier et al., 2014, Lang et al., 2014, Repka et al., 2007, Crowley et al., 2007, DiNunzio et al., 2010a, DiNunzio et al., 2010b, DiNunzio et al., 2010c, DiNunzio et al., 2010d, Hughey et al., 2010, Hughey et al., 2011, LaFountaine et al., 2016b, and Prasad et al., 2016, all of which are incorporated herein by reference. In some embodiments of these present disclosure, the pharmaceutical compositions may be prepared using a thermal process such as hot melt extrusion or hot melt granulation. In other embodiments, a fusion based process including thermokinetic mixing process such as those described at least in U.S. Pat. Nos. 8,486,423 and 9,339,440, the entire contents of which are herein incorporated by reference.

A non-limiting list of instruments which may be used to thermally process the pharmaceutical compositions described herein include hot melt extruders available from ThermoFisher®, such as a minilab compounder, or Leistritz®, such as a twin-screw extruder. Alternatively, a fusion-based high energy process instrument that does not require external heat input, including such as a thermokinetic mixer as described in U.S. Pat. Nos. 8,486,423 and 9,339,440 may be used to process the pharmaceutical composition.

In some aspects, the extruder may comprise heating the composition to a temperature from about 60° C. to about 300° C. In some embodiments, the temperature is from about 150° C. to about 250° C. The temperature that may be used is from about 60° C., 65° C., 70° C., 75° C., 80° C., 90° C., 92° C., 94° C., 96° C., 98° C., 100° C., 102° C., 104° C., 106° C., 108° C., 110° C., 112° C., 114° C., 116° C., 118° C., 120° C., 125° C., 130° C., 135° C., 140° C., 145° C., 150° C., 155° C., 160° C., 165° C., 170° C., 175° C., 180° C., 190° C., 200° C., 210° C., 220° C., 225° C., 230° C., 240° C., 250° C., 260° C., 270° C., 280° C., 290° C., to about 300° C. or any range derivable therein.

The extrudate produced following the extrusion process will generally comprise the active agent and the pharmaceutically acceptable polymer. The extrudate may be in the form of granules of a desired mesh size or diameter, rods that can be cut and shaped into tablets, and films of a suitable thickness that shaped forms can be punched into suitable size and shape for administration. This extrudate may be used in further processing steps to yield the final pharmaceutical product or composition. The extrudate of the pharmaceutical composition may be dried, formed, milled, sieved, or any combination of these processes to obtain a final composition which may be administered to a patient. Such processes are routine and known in the art and include formulating the specific product to obtain a final pharmaceutical or nutraceutical product. Additionally, the extrudate of the pharmaceutical composition obtained may be processed using a tablet press to obtain a final tablet. Additionally, it may be milled and combined with one or more additional excipients to form a capsule or pressed into a tablet. The resultant pharmaceutical composition may also be dissolved in a solvent to obtain a syrup, a suspension, an emulsion, or a solution.

B. Micronization and Jet Milling

As used in this application, the pharmaceutical composition may be "micronize" or "micronized" which refers to a substance, such as an active agent, that has been broken down into very fine particles, typically less than 10 μm, preferably between 0.5 and 5 um, more preferably between 1 and 3 um. A substance may be micronized by milling, grinding, or crushing. Milling may be performed by any method known in the art, such as by air jet mill, ball mill, wet mill, high pressure homogenization, or cryogenic mill.

In some aspects, "air jet mill" which is a device or method for reducing particle size by using a jet of compressed gas to impact particles into one another or the walls of the mill, thereby pulverizing the particles. An air jet mill may be used to micronize particles. Air jet mills are commercially available, such as the Aljet Model 00 Jet-O-Mizer™ (Fluid Energy, Telford, PA).

Alternatively, the pharmaceutical composition may be subjected to a "ball mill" which is a device or method for reducing particle size by adding the particle of interest and a grinding medium to the interior of a cylinder and rotating the cylinder. The particles of interest are broken down as the grinding medium rises and falls along the exterior of the cylinder as it rotates.

Furthermore, the pharmaceutical composition may be subjected to a "wet mill" or "media mill" which is a device or method for reducing particle size by adding the particle of interest to device with an agitator, containing a media comprising a liquid and a grinding medium. With the addition of the particle of interest, as the agitator rotates, the energy it disperses causes the grinding medium and particles of interest to come into contact and break down the particles of interest.

In other embodiments, the pharmaceutical composition may be subjected to a "high pressure homogenization" which is a device or a method of reducing particle size by adding the particle of interest to a device which combines both pressure and mechanical forces to break down the particle of interest. Mechanical forces used in high pressure homogenization may include impact, shear, and cavitation, among others.

As used herein in the specification and the claims, the term "cryogenic mill" refers to a device or method for reducing particle size by first chilling a particle of interest with dry ice, liquid nitrogen, or other cryogenic liquid, and subsequently milling the particle of interest to reduce the size.

C. Thin Film Freezing

Thus, in one aspect, the present disclosure provides pharmaceutical compositions which may be prepared using a thin-film freezing process. Methods of preparing pharmaceutical compositions using thin film freezing are described in U.S. Patent Application No. 2010/0221343, Watts, et al., 2013, Engstrom et al. 2008, Wang er al. 2014, Thakkar at el. 2017, O'Donnell er al. 2013, Lang er al. 2014a, Lang er al. 2014b, Carvalho er al. 2014, Beinborn er al. 2012a, Beinborn er al. 2012b, Zhang er al. 2012, Overhoff er al. 2009, Overhoff er al. 2008, Overhoff er al. 2007a, Overhoff er al. 2007b, Watts er al. 2010, Yang er al. 2010, DiNunzio er al. 2008, Purvis er al. 2007, Liu er al. 2015, Sinswat er al. 2008, and U.S. Pat. No. 8,968,786, all of which are incorporated herein by reference. In some embodiments, these methods involve dissolving the components of the pharmaceutical composition into a solvent to form a pharmaceutical mixture. The solvents may be either water or an organic solvent. Some non-limiting examples of organic solvents which may be used include volatile organic solvent such as 1,4-dioxane, acetonitrile, acetone, methanol, ethanol, isopropanol, dichloromethane, chloroform, tetrahydrofuran, tert-butyl alcohol, dimethyl sulfoxide, N,N-dimethyl formamide, diethyl ether, ethyl acetate, isopropyl acetate, butyl acetate, propyl acetate, toluene, hexanes, heptane, pentane, or combinations thereof. In some embodiments, the pharmaceutical mixture may contain less than 100 mg/mL of the therapeutic agent and excipient. The pharmaceutical mixture may contain less than 100, 90, 80, 70, 60, 50, 40, 30, 20, 17.5, 15, 12.5, 10, 7.5, 5, 2.5, or 1 mg/mL, or any range derivable therein.

This pharmaceutical mixture may be deposited on a surface which is at a temperature that causes the pharmaceutical mixture to freeze. In some embodiments, this temperature may be below the freezing point of the solution at ambient pressure. In other embodiments, a reduced pressure may be applied to the surface causing the solution to freeze at a temperature below the ambient pressure's freezing point. The surface may also be rotating or moving on a moving conveyer-type system thus allowing the pharmaceutical mixture to distribute evenly on the surface. Alternatively, the pharmaceutical mixture may be applied to surface in such a manner to generate an even surface.

After the pharmaceutical mixture has been applied to the surface, the solvent may be removed to obtain a pharmaceutical composition. Any appropriate method of removing the solvent may be applied including evaporation under reduced pressure or elevated temperature or lyophilization. In some embodiments, the lyophilization may comprise a reduced pressure and/or a reduced temperature. Such a reduced temperature may be from 25° C. to about −200° C., from 20° C. to about −175° C., from about 20° C. to about −150° C., from 0° C. to about −125° C., from −20° C. to about −100° C., from −75° C. to about −175° C., or from −100° C. to about −160° C. The temperature is from about −20° C., −30° C., −35° C., −40° C., −45° C., −50° C., −55° C., −60° C., −70° C., −80° C., −90° C., −100° C., −110° C., −120° C., −130° C., −140° C., −150° C., −160° C., −170° C., −180° C., −190° C., to about −200° C., or any range derivable therein. Additionally, the solvent may be removed at a reduced pressure of less than 500 mTorr, 450 mTorr, 400 mTorr, 375 mTorr, 350 mTorr, 325 mTorr, 300 mTorr, 275 mTorr, 250 mTorr, 225 mTorr, 200 mTorr, 175 mTorr, 150 mTorr, 125 mTorr, 100 mTorr, 75 mTorr, 50 mTorr, or 25 mTorr, or removed at a reduced pressure at any range of pressures derivable therein.

Such as composition prepared using these methods may exhibit a brittle nature such that the composition is easily sheared into smaller particles when processed through a device. These compositions have a low bulk or tapped density and have high surface areas as well as exhibit improved flowability of the composition. Such flowability may be measured, for example, by the Carr index or other similar measurements. In particular, the Carr's index may be measured by comparing the bulk density of the powder with the tapped density of the powder. Such compounds may exhibit a favorable Carr index and may result in the particles being better sheared to give smaller particles when the composition is processed through a secondary device to deliver the drug.

III. Definitions

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

As used herein, the terms "drug", "pharmaceutical", "active agent", "therapeutic agent", and "therapeutically active agent" are used interchangeably to represent a compound which invokes a therapeutic or pharmacological effect in a human or animal and is used to treat a disease, disorder, or other condition. In some embodiments, these compounds have undergone and received regulatory approval for administration to a living creature.

The use of the term "or" in the claims is used to mean "and/or" unless explicitly indicated to refer to alternatives only or the alternatives are mutually exclusive. As used herein "another" may mean at least a second or more.

The terms "compositions," "pharmaceutical compositions," "formulations," "pharmaceutical formulations," "preparations", and "pharmaceutical preparations" are used synonymously and interchangeably herein.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "derivative thereof" refers to any chemically modified polysaccharide, wherein at least one of the monomeric saccharide units is modified by substitution of atoms or molecular groups or bonds. In one embodiment, a derivative thereof is a salt thereof. Salts are, for example, salts with suitable mineral acids, such as hydrohalic acids, sulfuric acid or phosphoric acid, for example hydrochlorides, hydrobromides, sulfates, hydrogen sulfates or phosphates, salts with suitable carboxylic acids, such as optionally hydroxylated lower alkanoic acids, for example acetic acid, glycolic acid, propionic acid, lactic acid or pivalic acid, optionally hydroxylated and/or oxo-substituted lower alkanedicarboxylic acids, for example oxalic acid, succinic acid, fumaric acid, maleic acid, tartaric acid, citric acid, pyruvic acid, malic acid, ascorbic acid, and also with aromatic, heteroaromatic or araliphatic carboxylic acids, such as benzoic acid, nicotinic acid or mandelic acid, and salts with suitable aliphatic or aromatic sulfonic acids or N-substituted sulfamic acids, for example methanesulfonates, benzenesulfonates, p-toluenesulfonates or N-cyclohexylsulfamates (cyclamates).

The term "dissolution" as used herein refers to a process by which a solid substance, here the active ingredients, is dispersed in molecular form in a medium. The dissolution rate of the active ingredients of the pharmaceutical dose of the invention is defined by the amount of drug substance that goes in solution per unit time under standardized conditions of liquid/solid interface, temperature and solvent composition.

As used herein, the term "aerosols" refers to dispersions in air of solid or liquid particles, of fine enough particle size and consequent low settling velocities to have relative airborne stability (See Knight, V., Viral and Mycoplasmal Infections of the Respiratory Tract. 1973, Lea and Febiger, Phila. Pa., pp. 2).

As used herein, "inhalation" or "pulmonary inhalation" is used to refer to administration of pharmaceutical preparations by inhalation so that they reach the lungs and in particular embodiments the alveolar regions of the lung. Typically inhalation is through the mouth, but in alternative embodiments in can entail inhalation through the nose.

As used herein, "dry powder" refers to a fine particulate composition that is not suspended or dissolved in an aqueous liquid.

A "simple dry powder inhaler" refers a device for the delivery of medication to the respiratory tract, in which the medication is delivered as a dry powder in a single-use, single-dose manner. In particular aspects, a simple dry powder inhaler has fewer than 10 working parts. In some aspects, the simple dry powder inhaler is a passive inhaler such that the dispersion energy is provided by the patient's inhalation force rather than through the application of an external energy source.

A "median particle diameter" refers to the geometric diameter as measured by laser diffraction or image analysis. In some aspects, at least either 50% or 80% of the particles by volume are in the median particle diameter range.

A "Mass Median Aerodynamic Diameter (MMAD)" refers to the aerodynamic diameter (different than the geometric diameter) and is measured by laser diffraction.

The term "amorphous" refers to a noncrystalline solid wherein the molecules are not organized in a definite lattice pattern. Alternatively, the term "crystalline" refers to a solid wherein the molecules in the solid have a definite lattice pattern. The crystallinity of the active agent in the composition is measured by powder x-ray diffraction.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

As used in this specification, the term "significant" (and any form of significant such as "significantly") is not meant to imply statistical differences between two values but only to imply importance or the scope of difference of the parameter.

Throughout this application, the term "about" is used to indicate that a value includes the inherent variation of error for the device, the method being employed to determine the value, or the variation that exists among the study subjects or experimental studies. Unless another definition is applicable, the term "about" refers to t5% of the indicated value.

As used herein, the term "substantially free of" or "substantially free" in terms of a specified component, is used herein to mean that none of the specified component has been purposefully formulated into a composition and/or is present only as a contaminant or in trace amounts. The total amount of all containments, by-products, and other material is present in that composition in an amount less than 2%. The term "essentially free of" or "essentially free" is used to represent that the composition contains less than 1% of the specific component. The term "entirely free of" or "entirely free" contains less than 0.1% of the specific component.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements and parameters.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

IV. Examples

To facilitate a better understanding of the present disclosure, the following examples of specific embodiments are given. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure. In no way should the following examples be read to limit or define the entire scope of the disclosure.

Example 1—Oral Formulations of Niclosamide as Amorphous Solid Dispersion

A. Preparation of Oral Formulation

The formulations were processed using a HAAKE Minilab II microextruder with a screw speed of 150 rpm at 180° C. The cooled extrudates were milled into granules and particles retained on a 45 μm sieve but that passed through a 150 μm sieve were used for further testing. Dissolution tests were conducted on polymer-niclosamide extrudates at different drug loadings in a Hanson SR8-Plus apparatus (Hanson Research Co., USA) using the 200 mL vessels and their paddles. FaSSIF medium (Biorelevant.com Ltd., UK)

was prepared according to manufacturer specifications. Formulations containing 80 mg of niclosamide were added into 150 mL of FaSSIF medium, the apparatus was set at 37.0±0.5° C. and 100 rpm. The sampling times were 5, 10, 15, 30, 60, and 120 minutes. When recollecting the samples, these were passed through 0.2 µm filters. Then, 0.5 mL of the samples were mixed with 1 mL of acetone and 0.5 mL of acetonitrile for HPLC analysis.

B. HPLC Analysis

The samples were measured at 331 nm using a Dionex® HPLC system (Thermo Fisher® Scientific Inc., USA) with a ZORBAX® SB-C18 column (4.6×250 mm, 5 µm) (Agilent®, USA) at 1 mL/min flow rate. Two mobile phases were used, the mobile phase A was formic acid water solution at 0.3%, and the mobile phase B was acetonitrile, they were mixed in a 40:60 ratio.

C. Dissolution Analysis for Oral Formulations

Figure 1:
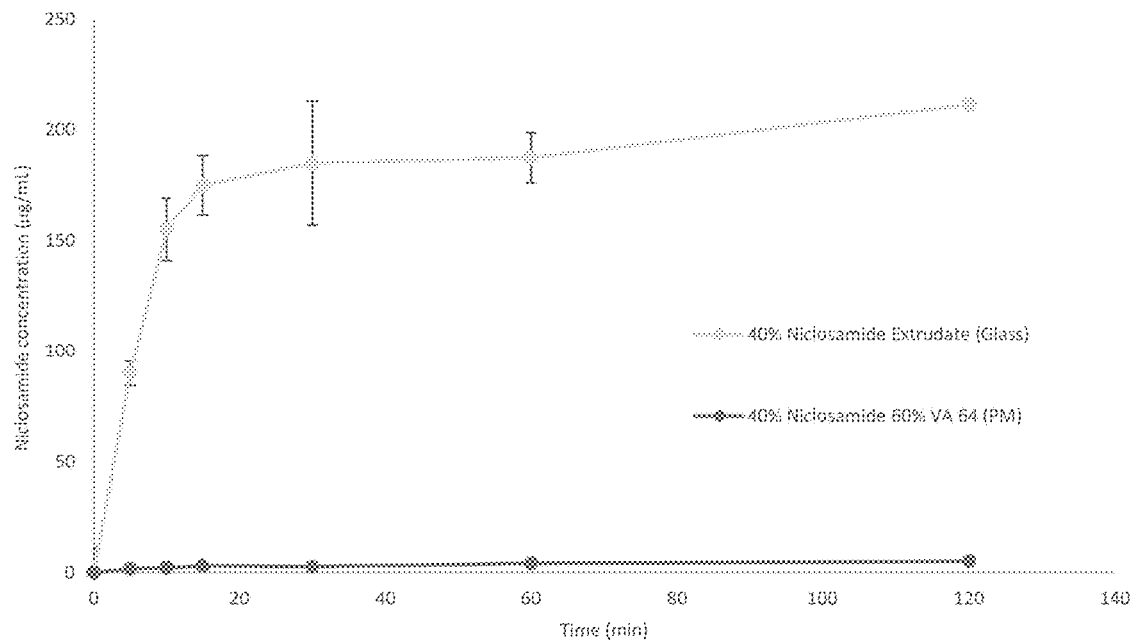
FIG. 1 shows the dissolution test of Niclosamide 40%-VA64® 60% extrudate (amorphous/glass) and physical mixture (PM).
Figure 2:
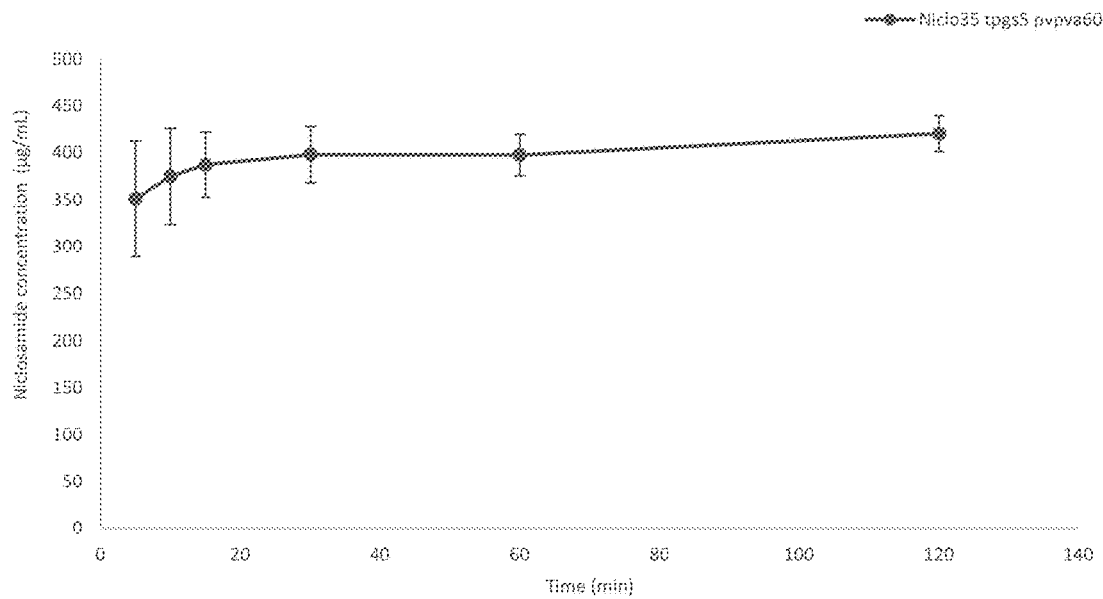
FIG. 2 shows the dissolution test of Niclosamide 35%-VA64® 60%-TPGS 5% extrudate.
Figure 3:
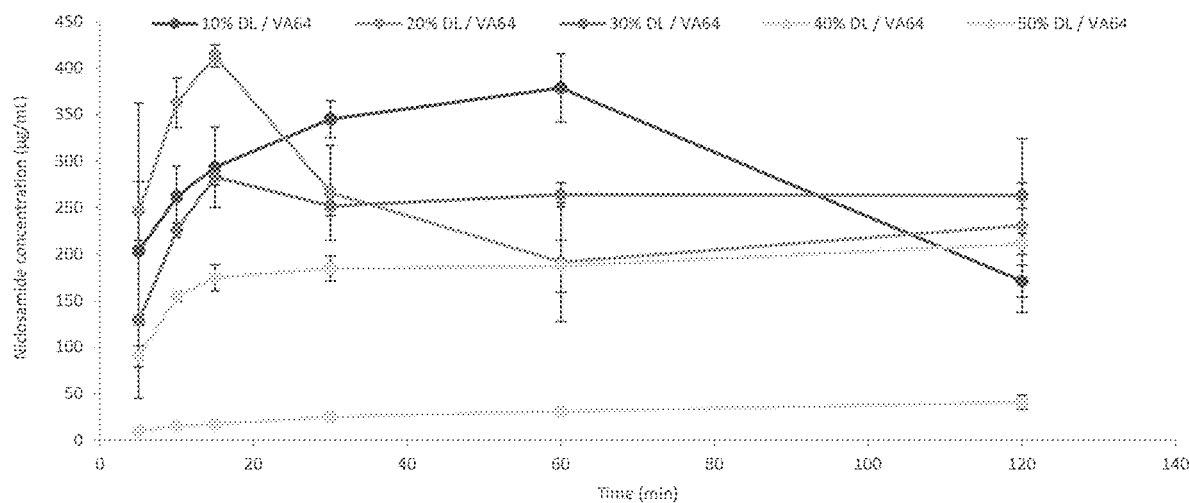
FIG. 3 shows the dissolution test of Niclosamide-VA64® extrudates at different drug loadings (DL).
Figure 4:
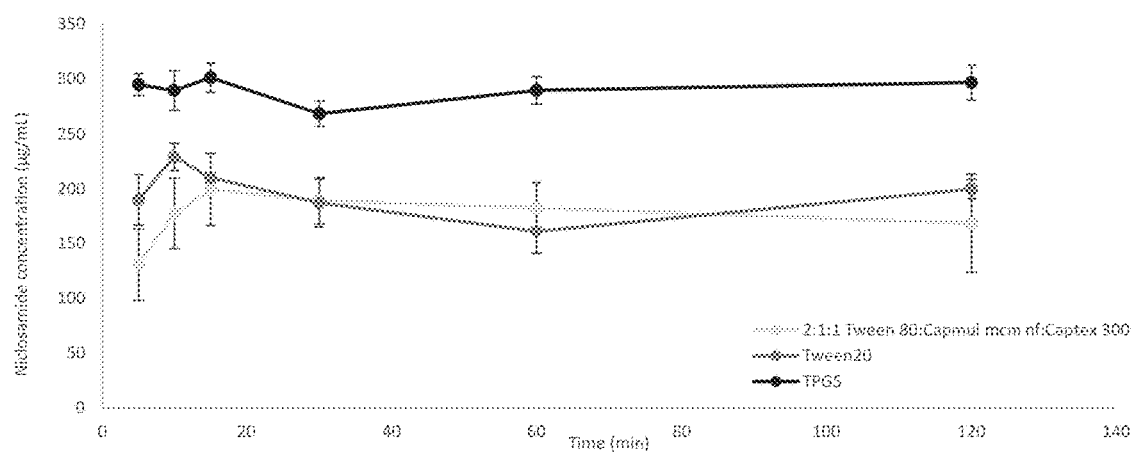
FIG. 4 shows the dissolution test of Niclosamide 20%-VA64® 75%-5% surfactant/emulsifiers.
Figure 5:
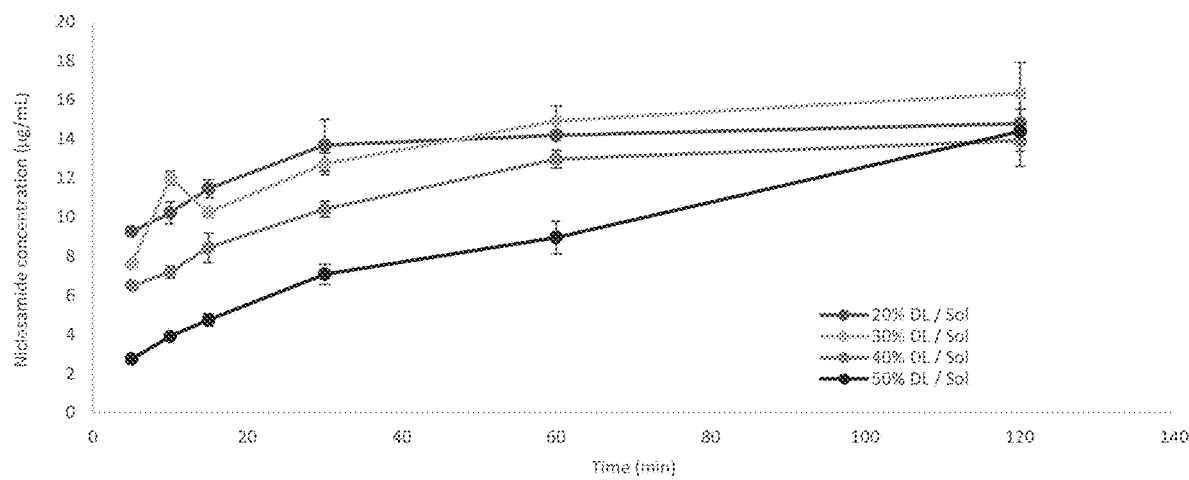
FIG. 5 shows the dissolution test of Niclosamide-Soluplus® (Sol) extrudates at different drug loadings (DL).
Figure 6:
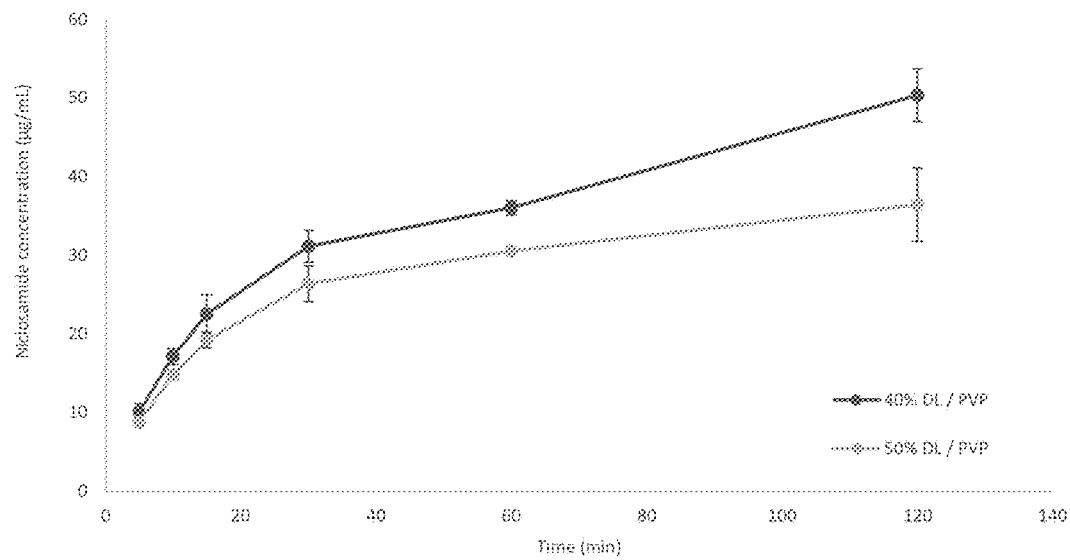
FIG. 6 shows the dissolution test of Niclosamide-Kollidon 30® (polyvinylpyrrolidone) at 40 and 50% drug loading (DL).

A sample of Kollidon VA64® with niclosamide was physically mixed and another sample was process through a hot melt extruder as described in above. These two samples were subjected to HPLC analysis to determine the dissolution of the drug in the composition. The HPLC analysis showing significant dissolution of niclosamide into the composition are shown in FIG. 1. Then, the amount of drug in the composition was varied between 10% drug load and 50% drug load which all showed high dissolution of niclosamide in the extrudate (FIG. 3). Several surfactant compositions were tested to determine their ability to maintain the niclosamide concentration in the dissolution assay. FIG. 4 shows that all three composition showed the ability to retain the niclosamide but the composition with TPGS showed the highest overall dissolution. Finally, decreasing the drug load to 35% while maintaining TPGS at 5% of showed high dissolution which persisted over 2 hours. See FIG. 2. Two other polymer excipients were tested (Kollidon 30® and SolvPlus®) which showed dissolution of niclosamide but at a lower extent than Kollidon VA64® (FIGS. 5 & 6).

D. Pharmacokinetic Evaluation of Milled Niclosamide Extrudate

Figure 7:
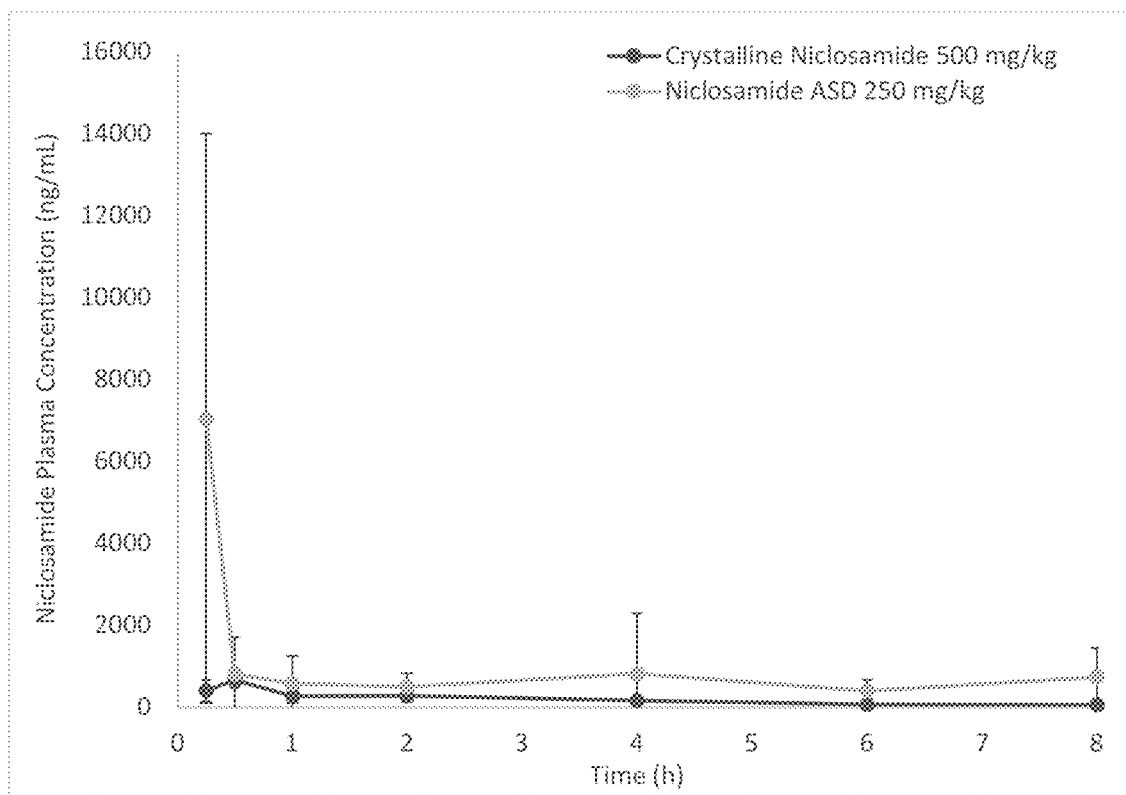
FIG. 7 shows the niclosamide plasma concentration as a function of time in mice dosed with the niclosamide amorphous solid dispersion compared to crystalline niclosamide.

CD-1 mice were dosed with either crystalline niclosamide at a dose of 500 mg/kg suspended in 0.5% Methocel A4M in a volume corresponding to 10 ml/kg or with milled niclosamide extrudate at a dose of 250 mg/kg suspended in pH 6.5 FaSSIF media (Biorelevant.com Ltd) in a volume corresponding to 10 mL/kg. The pH 6.5 FaSSIF media was prepared as instructed with the exception of the buffer salts, sodium hydroxide and sodium phosphate monobasic anhydrous, being present at two-fold their instructed concentration. Plasma samples from mice were taken at 0.25, 0.5, 1, 2, 4 6, and 8 h after administration and analyzed by LC/MS/MS for niclosamide concentration. See the data shown in FIG. 7 and Table 1.

TABLE 1

Pharmacokinetic Data for ASD formulation of Nicolsamide

| PK Parameter | Crystalline Nic (500 mg/kg) | Nic ASD (250 mg/kg) |
|---|---|---|
| Cmax (ng/mL) | 661.7 | 7048.0 |
| Tmax (h) | 0.5 | 0.25 |
| AUC0-last (ng *h/mL) | 1454.6 | 6375.5 |

D. Particle Size Analysis During Dissolution

Samples taken from the dissolution vessel were centrifuged at 13,000 rpm (14,300 rcf) for 10 min. Then, the supernatant was measured using a Zetasizer Nano ZS (Malvern Instruments Ltd., Worcestershire, UK). The dispersant was water, and the samples were equilibrated at 37° C. before being measured using the 173° backscatter with automatic measurement duration in triplicate (FIG. 8).

Side-by-side diffusion cells (PermeGear, Hellertown, PA, USA) were employed to evaluate the diffusion of the niclosamide ASD through a 0.03 µm polyethersulfone membrane (Sterlitech Corp., Kent, WA, USA). The donor and receiver cells were filled with 34 mL of FaSSIF and decanol, respectively. 52.1 mg of the niclosamide ASD and 18.2 mg of niclosamide anhydrate was added to the donor cell at 37° C. and 850 rpm. The samples were collected from the receiver cell at 5, 10, 15, 30, 60, 120, and 180 min. Samples were measured using the same HPLC method described above. See FIG. 9.

The pH-shift dissolution tests were performed using the same equipment in two stages. First, 230 mg of niclosamide ASD was poured in 30 mL of HCl 0.01 M for 30 min. Thereafter, 150 mL of FaSSIF was added into the vessel, completing a volume of 180 mL, and the samples were taken at the same time points of the previously described dissolution test. When required, to separate the particles and the unbound drug from the samples, an Airfuge™ Air-Driven Ultracentrifuge (Beckman Coulter, Palo Alto, CA, USA) was used at 30 psi for 30 min. Then, the supernatant was measured using HPLC. See FIG. 10.

E. Animal Studies

The oral pharmacokinetic analysis was conducted at Pharmaron (Ningbo, China). The study protocol was approved and conducted in accordance with the Institutional Animal Care and Use Committee (IACUC) guidelines at Pharmaron. (IACUC; Protocol Number AUP-PK-R-06012019). In this study, niclosamide anhydrate and niclosamide ASD were administered to five rats per group (weight=205.8±2.9 g each) at a niclosamide dose of 10 mg/kg by oral gavage. The groups received a FaSSIF suspension of niclosamide anhydrate at 1.5 mg/mL, a FaSSIF suspension of niclosamide ASD at 1.5 mg/mL, and size 9 mini capsules (Braintree Scientific, Braintree, MA, USA) containing niclosamide ASD, respectively (three groups in total). In this last group, the capsule size 9 contained 60% niclosamide ASD, 15% EXPLOTAB®, and 25% sodium bicarbonate. The powders were blended by mortar and pestle and loaded into the capsules using the capsule filling funnel for size 9 (Torpac, Fairfield, NJ, USA). The samples were measured using an AB Sciex Triple Quad 5500 LC/MS/MS with an Agilent Eclipse® XDB-C18 column (2.1×150 mm, 5 µm) (Agilent, Palo Alto, CA, USA) at a flow rate of 0.6 mL/min. Two mobile phases were used. The mobile phase A was a 0.1% formic acid aqueous solution, and the mobile phase B was a mixture of 5% water and 95% acetonitrile (0.1% formic acid). They were mixed as shown in Table 2. Then, 50 µL of plasma with 5 µL of methanol were added to 200 µL of methanol containing an internal standard mixture for protein precipitation. The samples were vortexed for 30 s and underwent centrifugation for 15 min at 4000 rpm and ° C. Thereafter, the supernatant was diluted three times with water, and 2 µL were injected into the HPLC. The results of the pharmacokinetic profile studies are shown in FIG. 11 and Table 3. Furthermore, the resultant particles were subjected to dissolution and the resultant supernatants after centrifugation were analyzed. From this data, it can be noted that dissolution in FaSSIF helps in the generation of smaller nanoparticles. See Table 4.

TABLE 2

Mobile phase gradient that was used for analyzing plasma sample.

| Time (min) | A (%) | B (%) |
|---|---|---|
| 0.20 | 85.0 | 15.0 |
| 2.00 | 50.0 | 50.0 |
| 2.50 | 50.0 | 50.0 |
| 4.00 | 0.00 | 100 |
| 4.50 | 0.00 | 100 |
| 4.51 | 85.0 | 15.0 |
| 5.00 | 85.0 | 15.0 |

TABLE 3

Pharmacokinetic parameter profiles (in rats) of niclosamide anhydrate suspended in FaSSIF, niclosamide ASD suspended in FaSSIF, and niclosamide ASD in capsules (n = 5).

| PK parameters | Niclosamide anhydrate suspension in FaSSIF | Niclosamide ASD suspension in FaSSIF | Niclosamide ASD in capsules |
|---|---|---|---|
| $T_{1/2\ (h)}$ | 1.00 (0.30) | 1.59 (1.34) | 0.84 (0.01) |
| $T_{max\ (h)}$ | 3.60 (0.89) | 2.40 (1.52) | 4.40 (0.89) |
| $C_{max\ (ng/mL)}$ | 48.3 (20.6) | 123 (56) | 122 (71) |
| $AUC_{last\ (h*ng/mL)}$ | 168 (64) | 398 (115) | 338 (193) |
| $AUC_{Inf\ (h*ng/mL)}$ | 188 (84) | 495 (239) | 463 (224) |
| $AUC_{\%\ Extrap}$—obs (%) | 8.4 (7.0) | 12.2 (21.4) | 7.98 (0.48) |
| $MRT_{Inf}$—obs (h) | 3.56 (0.70) | 3.71 (2.20) | 4.04 (0.12) |
| $AUC_{last}/D$ (h*mg/mL) | 16.8 (6.4) | 39.8 (11.5) | 33.8 (19.3) |

TABLE 4

Mean particle size, PDI, and zeta potential of supernatants after centrifugation at 13,000 rpm × 10 min. The samples were taken from the dissolution apparatus at different time points.

| Sample | Sampling time (h) | Mean particle size (d · nm) | PDI | Zeta potential (mV) |
|---|---|---|---|---|
| FaSSIF media | 1 | 66.5 ± 0.9 | 0.037 ± 0.048 | −14.8 ± 2.3 |
| Extrudate niclosamide 35% - TPGS 5% - PVP 60% in Buffer 6.5 | 1 | 228.1 ± 4.2 | 0.157 ± 0.011 | −12.1 ± 0.1 |
| Extrudate niclosamide 35% - TPGS 5% - PVP 60% in FaSSIF | 1 | 99.3 ± 1.4 | 0.224 ± 0.004 | −13.6 ± 1.0 |

Example 2—Inhalation Formulations of Niclosamide

A. Micronized Niclosamide Formulations

Niclosamide bulk powder was air jet milled in a lab-scale Aljet® air jet mill (also known as a model 00 Jet-O-Mizer, Fluid Energy, Telford, PA) to a particle size distribution within the respirable range. The air jet mill was set at 80 psi grind pressure (both nozzles), 80 psi feed pressure, and less than 1 g/min feed rate (0.5-1 g/min). In one batch the powder was collected using a cyclone and collection vessel. In a second batch the powder was milled directly into a collection bag without the cyclone. An exemplary jet mill is shown in FIG. 12.

The particle size and dispersion characteristics were then assessed. Geometric particle size distribution for each milled batch was assessed with a HELOS laser diffraction instrument (Sympatec GmbH, Germany) using RODOS dispersion at 1, 2, and 3 bar dispersion pressures. Measurements were taken every 5-10 ms following powder dispersion and trigger activation. Measurements that were between 5 and 25% optical density were averaged to determine particle size distribution. Table 5 shows the results of the analysis. Illustrative particle size distribution of micronized niclosamide dispersed using Rodos at 1 Bar dispersion pressure. See, also, FIG. 13.

TABLE 5

Micronized Particle Characterization and Dispersion
Niclosamide Micronized Powder Dispersion

| | Dispersion Pressure (Bar) | X10 | X50 | X90 | X99 | VMD | COPT |
|---|---|---|---|---|---|---|---|
| Un-Milled | 1 | 2.15 | 11.62 | 58.54 | 125.23 | 22.25 | 15.36 |
| | 1 | 2.11 | 11.22 | 56.87 | 128.57 | 21.69 | 15.69 |
| | Mean | 2.13 | 11.42 | 57.705 | 126.9 | 21.97 | |
| | Dispersion Ratio | 1 | 1 | 1 | 1 | 1 | |
| | 2 | 1.69 | 9.24 | 49.26 | 119.41 | 18.66 | 13.25 |
| | 2 | 1.63 | 8.94 | 48.08 | 126.35 | 18.37 | 11.87 |
| | Mean | 1.66 | 9.09 | 48.67 | 122.88 | 18.515 | |
| | Dispersion Ratio | 0.78 | 0.80 | 0.84 | 0.97 | 0.84 | |
| | 3 | 1.47 | 7.95 | 41.71 | 95.36 | 15.73 | 12.27 |
| | 3 | 1.46 | 7.95 | 41.12 | 98.89 | 15.65 | 12.82 |
| | Mean | 1.465 | 7.95 | 41.415 | 97.125 | 15.69 | |
| | Dispersion Ratio | 0.69 | 0.70 | 0.72 | 0.77 | 0.71 | |

TABLE 5-continued

| Micronized Particle Characterization and Dispersion Niclosamide Micronized Powder Dispersion | | | | | | | |
|---|---|---|---|---|---|---|---|
| | Dispersion Pressure (Bar) | X10 | X50 | X90 | X99 | VMD | COPT |
| Micronized | 1 | 1.44 | 3.17 | 5.9 | 8.97 | 3.49 | 17.65 |
| | 1 | 1.43 | 3.15 | 5.89 | 8.98 | 3.47 | 14.82 |
| | Mean | 1.435 | 3.16 | 5.895 | 8.975 | 3.48 | |
| | Dispersion Ratio | 1.00 | 1.00 | 1.00 | 1.00 | 1.00 | |
| | 2 | 1.24 | 2.78 | 5.3 | 8.22 | 3.07 | 14.65 |
| | 2 | 1.23 | 2.77 | 5.3 | 8.28 | 3.07 | 14.43 |
| | Mean | 1.235 | 2.775 | 5.3 | 8.25 | 3.07 | |
| | Dispersion Ratio | 0.86 | 0.88 | 0.90 | 0.92 | 0.88 | |
| | 3 | 1.16 | 2.65 | 5.08 | 7.9 | 2.94 | 14.15 |
| | 3 | 1.08 | 2.6 | 5.1 | 7.99 | 2.9 | 19.08 |
| | Mean | 1.12 | 2.625 | 5.09 | 7.945 | 2.92 | |
| | Dispersion Ratio | 0.78 | 0.83 | 0.86 | 0.89 | 0.84 | |
| 2nd Batch Micronized | 2 | 1.03 | 3 | 6.4 | 10.55 | 3.44 | 15.51 |
| | 2 | 0.95 | 2.74 | 6 | 25.61 | 3.58 | 14.15 |
| | Mean | 0.99 | 2.87 | 6.2 | 18.08 | 3.51 | |

In vitro aerodynamic performance testing was performed utilizing a medium resistance Monodose RSO1 DPI, a gift from Plastiape S.p.a (Osnago, Italy). Size 3 hydroxypropyl methylcelllulose (HPMC) capsules were provided by ACG. The resistance of the RSO1 Monodose DPI used in the cascade impaction studies was determined using a dosage sampling unit according to apparatus B of USP Chapter 601, and was calculated to be 0.22 kPaO.5 min/L. Cascade impaction studies for milled niclosamide were performed on the Next Generation Impactor (NGI) (MSP Corporation, MN, USA). Stage 1-7 cutoff diameters were determined using eq 1, and MOC cutoff diameters were determined using eq 2:

$$D_{50,Q} = D_{50,Q}\left(\frac{Q_n}{Q}\right)^X \quad (1)$$

$$D_{50,Q} = 0.14\left(\frac{Q_n}{Q}\right)^{1.36} \quad (2)$$

where D50, Q is the cutoff diameter at the flow rate, Q, and the subscript, n, refers to the archival reference value for Qn=60 L/min, and the values for the exponent, X, refer to the archival NGI stage cut size-flow rate calculations as determined by Marple et al. To reduce particle bounce and re-entrainment, the NGI plates were coated with 1% (v/v) glycerin in ethanol and allowed to dry.

Cascade impaction was performed on these samples at a 4 kPa pressure drop (equivalent to 88 L/min on the medium-resistance RSO1 device) at a duration of time sufficient to draw 4 L of air through the apparatus (2.7 s), according to USP specifications. To determine the flow rate dependency of milled niclosamide dispersion, cascade impaction was also performed at a 2 kPa pressure drop through the device (equivalent to 64 L/min) for a duration of 3.8 s.

The resultant dispersed powder was collected from the capsule, the adapter, the induction port, stages 1-7, and the micro-orifice collector (MOC) by washing with 80% acetonitrile: 20% deionized water. Powder was collected from the inhaler device using swabs wetted with water followed by rinsing and dilution of the swabs with the 80% acetonitrile: 20% deionized water solution. The drug mass in each sample was quantified by measuring the UV absorbance at a wavelength of 331 nm using a Tecan Infinite1 200 PRO multimode microplate reader (Tecan Systems, Inc., San Jose, CA, USA). The emitted fraction (EF) was calculated as the total drug emitted from the device as a percentage of the total mass of drug collected. The fine particle (<5 μm) fraction (FPF5 μm/EF) and fine particle (<3 μm) fraction (FPF3 μm/EF) corresponded to the percentage of the emitted dose predicted to have the aerodynamic diameter below 5 and 3 μm. The Fine Particle Dose (FPD) is the total mass of drug collected from plates predicted to have aerodynamic diameters below 5 and 3 μm. The FPF5 μm/EF and FPF3 μm/EF values were interpolated from a graph with the cumulative percentage of the emitted dose deposited downstream from an NGI stage as the ordinate and the particle cutoff size of that stage as the abscissa.

For each sample, the mass median aerodynamic diameter (MMAD), which represents the mass-based median point of the aerodynamic particle size distribution (APSD), and geometric standard deviation (GSD), which represents the spread of the APSD, were determined by plotting the cumulative percentage of mass less than the stated aerodynamic size cut (expressed as Probits) against the aerodynamic diameter (log scale). Distributions were log-normal. A linear regression was performed to determine the aerodynamic diameters corresponding to the 50% percentile (Probit 5) to determine the MMAD, and the aerodynamic diameters corresponding the 15.87% percentile (Probit 4) and 84.13% percentile (Probit 6) to calculate the GSD. These results are shown in Table 6.

TABLE 6

| Inhalation Properties of Micronized Niclosamide | | | | |
|---|---|---|---|---|
| | FPF 5 μm/ED (FPD 5 μm) | FPF 3 μm/ED (FPD 3 μm) | MMAD | GSD |
| Run1, 4 kPa | 52.8% (4154.3) | 40.1% (3154.9) | 3.19 | 2.01 |
| Run2, 4 kPa | 41.1% (2939.4) | 27.4% (1962.1) | 3.67 | 2.11 |
| Run3, 4 kPa | 47.2% (3398.1) | 27.4% (1975.2) | 3.50 | 2.04 |
| Run4, coated 4 kPa | 43.2% (2626.9) | 28.6% (1740.8) | 3.49 | 2.02 |
| 2 kPa | 30.54% (1828.2) | 20.09% (1202.8) | 5.39 | 2.34 |

Powder X-ray diffraction was obtained using a Miniflex® 600 (Rigaku, Woodlands, TX, USA) on the starting niclosamide material as well as the micronized material. The diffraction pattern was scanned from 5° to 40° at a step size of 0.02°/min and continuous scanning speed of 2°/min with an accelerating voltage of 40 kV and 15 mA. See FIG. 14.

i. Evaluation of Micronized Niclosamide in Reducing Viral Titers.

The effectiveness of micronized niclosamide was tested by seeding Vero cells into 6-well plate and infect with SARS-CoV-2. Then, prepare a 1 mg/mL suspension of the powder by weighing out 5 mg of the drug. About 5 mL of cell culture media was added inside a sterile environment. A dispersed suspension was generated using vortexing and sonication until all clumps of powder are broken up. The suspension was not filtered. The suspension may be centrifuged to reduce foaming but should be sonicated to redisperse particles prior to further dilutions. From this point forward, all work was carried out in a sterile environment. The NIC-M suspension was diluted 10× to generate 1 mL of a 100 µg/mL suspension (stock A). Then, dilute the 100 µg/mL suspension 10× to generate 1 mL of a 10 µg/mL suspension (stock B). From stock A and B, dilute to achieve the concentrations in the Table 7 below. Then, the cell culture media was replaced with the prepared suspensions as shown in FIG. 23A. The plate is prepared in triplicate. Then, the viral viability was tested 24 hours after dosing. The results from the treatment group are shown below in Table 8.

TABLE 7

Study design for in vitro evaluation of micronized NIC powder

| Group | NIC conc (µg/mL) |
|---|---|
| NIC-M-2 | 2.0 |
| NIC-M-1 | 1.0 |
| NIC-M-0.5 | 0.5 |
| NIC-M-0.25 | 0.25 |
| NIC-M-0.125 | 0.125 |

TABLE 8

Results of 24 hour exposure with NIC micronized powder

| NIC conc (µg/mL) | Average reduction in SARS-CoV-2 viral titers versus untreated control |
|---|---|
| 2 | 81.3 ± 7.0 |
| 1 | 46.6 ± 23.1 |
| 0.5 | 19.0 ± 13.7 |
| 0.25 | 99.6 ± 0.1 |
| 0.125 | 85.5 ± 5.1 |

B. Micronized Niclosamide Combination with Clofazimine

Further compositions of niclosamide with clofazimine were prepared. Niclosamide was micronized to a D50 cut-off diameter of 2.6 µm and a D90 cut-off diameter of 5.5 µm using a Model 00 Jet-O-Mizer air jet mill. Clofazimine was micronized to a D50 cut-off diameter of 2.2 µm and a D90 cut-off diameter of 5.1 µm. The powders were physically blended in the following mass ratios: 4:1 niclosamide-clofazimine, 1:1 niclosamide-clofazimine, and 1:9 niclosamide-clofazimine. Physical blending of the powders was performed using a Turbula blender for a length of time sufficient to result in a coefficient of variation percentage that was less than 5% for powder aliquots from the blend.

The aerosolization properties of these compositions are described in Table 9. In vitro aerodynamic studies were performed as previously described for the micronized niclosamide formulation.

TABLE 9

Micronized Compositions of Niclosamide and Clofazimine

| | Niclosamide | | | | Clofazimine | | | |
|---|---|---|---|---|---|---|---|---|
| | FPF 5 µm/ED (FPD 5 µm) | FPF 3 µm/ED (FPD 3 µm) | MMAD (µm) | GSD | FPF 5 µm/ED (FPD 5 µm) | FPF 3 µm/ED (FPD 3 µm) | MMAD (µm) | GSD |
| Niclosamide:Clofazimine 1:1 blend 4 kPa | 52.6% (3529.4) | 26.8% (1799.6) | 4.43 | 2.38 | 53.5% (2571.4) | 24.5% (1177.5) | 4.34 | 2.09 |
| Niclosamide:Clofazimine 1:1 blend 2 kPa | 58.3% (2998.4) | 32.7% (1681.3) | 4.08 | 2.36 | 62.6% (2598.1) | 34.4% (1427.0) | 4.43 | 1.99 |
| Niclosamide:Clofazimine 1:9 blend 4 kPa | 49.2% (955.0) | 30.3% (588.2) | 3.34 | 2.42 | 45.0% (1626.3) | 36.1% (1305.7) | 2.70 | 2.10 |
| Niclosamide:Clofazimine 1:9 blend 2 kPa | 57.7% (1296.5) | 35.8% (804.7) | 3.73 | 2.14 | 69.7% (3696.6) | 52.0% (2758.0) | 3.12 | 1.90 |
| Niclosamide:Clofazimine 1:4 blend 4 kPa | 57.4% (7146.5) | 32.8% (4082.4) | 3.57 | 2.10 | 45.0% (1930.0) | 36.1% (962.4) | 3.89 | 1.87 |
| Niclosamide:Clofazimine 1:4 blend 2 kPa | 46.5% (5795.4) | 22.5% (2800.3) | 5.54 | 2.32 | 45.7% (1384.7) | 16.9% (512.6) | 6.20 | 2.01 | ii. Evaluation of Niclosamide With Clofazimine Reducing Viral Titers.

The effectiveness of niclosamide with clofazimine was tested by seeding Vero cells into 6-well plate and infect with SARS-CoV-2 using a standard protocol. Then, a 1 mg/mL suspension of the 9:1 CFZ-NIC powder was prepared by weighing out 5 mg of the powder. To this, 5 mL of DMEM cell culture media was added inside a sterile environment. Generate a dispersed suspension using vortexing and sonication until all clumps of powder are broken up. The suspension was not filtered. The suspension can be centrifuged to reduce foaming but was be sonicated to redisperse particles prior to further dilutions. The suspensions were further diluted in DMEM to achieve the concentrations listed in Table 10. Then, the cell culture media replaced with the prepared suspensions according to FIG. 23B. The plate was prepared in triplicate. Viral viability was tested 24 hours after dosing.

TABLE 10

Study design for in vitro evaluation of 9:1 CFZ-NIC powder blend

| Group | NIC conc (µg/mL) | CFZ conc (µg/mL) |
| --- | --- | --- |
| 9:1 CFZ-NIC-2 | 2.0 | 38.0 |
| 9:1 CFZ-NIC-1 | 1.0 | 19.0 |
| 9:1 CFZ-NIC-0.5 | 0.5 | 9.5 |
| 9:1 CFZ-NIC-0.25 | 0.25 | 4.8 |
| 9:1 CFZ-NIC-0.125 | 0.125 | 2.4 |

Treatment with the highest concentration of the drugs (NIC dosed at 2 µg/mL and 1 µg/mL) resulted in cell death, so were not evaluated further. The results from the other treatment group are summarized in Table 11.

TABLE 11

Results of 24 hour exposure with 9:1 CFZ:NIC powder formulation

| NIC conc (µg/mL) | Average reduction in SARS-CoV-2 viral titers versus untreated control |
| --- | --- |
| 0.5 | 38.73 ± 31.50 |
| 0.25 | 97.81 ± 0.60 |
| 0.125 | 74.74 ± 12.52 |

C. Brittle Matrix Niclosamide Particles

Formulations of niclosamide with four different carbohydrates were prepared according to the table below. Niclosamide was dissolved in 1-4 dioxane. Separately, the respective carbohydrate was dissolved in deionized water. The two solutions were then mixed together in a glass vial and shaken until clear.

TABLE 12

Table of Components

| Component | i Trehalose | ii Lactose monohydrate | iii Mannitol | iv Sucrose |
| --- | --- | --- | --- | --- |
| Niclosamide (mg) | 80 | 80 | 80 | 80 |
| 1,4-dioxane (mL) | 16 | 16 | 16 | 16 |
| Water (mL) | 4 | 4 | 4 | 4 |
| Trehalose (mg) | 80 | — | — | — |
| Lactose Monohydrate (mg) | — | 80 | — | — |
| Mannitol (mg) | — | — | 80 | — |
| Sucrose (mg) | — | — | — | 80 |

Solutions i-iv were prepared by thin film freezing into frozen thin films by dropwise addition (at approximately 2 mL/min through a 19 gauge needle) to a rolling drum set at −80±10° C. at a height of 10 cm from the surface of the drum. Drum was rotating at 200 rpm with a blade to scrape off the frozen films after they were produced. Frozen films were immediately collected into liquid nitrogen and maintained at −80° C. until lyophilization. Primary drying during lyophilization was performed at −40° C. and 100 mTorr for 1200 minutes followed by ramping of the temperature to 25° C. over 1200 min for secondary drying. Secondary trying at 25° C. and 100 mTorr was performed over a minimum of 1200 min.

In vitro aerodynamic performance testing of formulations i-iv was performed by Next Generation Impaction testing (NGI). Testing of the formulations was conducted using an RS00 dry powder inhaler device by Plastiape S.p.a (Osnago, Italy) filled with 6.00+-0.18 mg of formulation at a flow rate sufficient to provide a 4 kPa pressure drop, 58 L/min, and for a sufficient amount of time to draw 4 L of air through the device, 4.2 sec.

The resultant dispersed powder was collected from the capsule, the adapter, the induction port, stages 1-7, and the micro-orifice collector (MOC) by washing with 80% acetonitrile: 20% deionized water. Powder was collected from the inhaler device using swabs wetted with water followed by rinsing and dilution of the swabs with the 80% acetonitrile: 20% deionized water solution. The drug mass in each sample was quantified by measuring the UV absorbance at a wavelength of 331 nm using a Tecan Infinite1 200 PRO® multimode microplate reader (Tecan Systems, Inc., San Jose, CA, USA). The emitted fraction (EF) was calculated as the total drug emitted from the device as a percentage of the total mass of drug collected. The fine particle (<5 µm) fraction (FPF5 µm/EF) and fine particle (<3 µm) fraction (FPF3 µm/EF) corresponded to the percentage of the emitted dose predicted to have the aerodynamic diameter below 5 and 3 µm. The FPF5 µm/EF and FPF3 µm/EF values were interpolated from a graph with the cumulative percentage of the emitted dose deposited downstream from an NGI stage as the ordinate and the particle cutoff size of that stage as the abscissa. The Fine Particle Dose (FPD) is the total mass of drug collected from plates predicted to have aerodynamic diameters below 5 and 3 µm. See Table 13.

TABLE 13

Dispersion Properties of the Brittle Matrix Pharmaceutical Composition

| | FPF 5 µm/ED (FPD 5 µm) | FPF 3 µm/ED (FPD 3 µm) | MMAD (µm) | GSD |
| --- | --- | --- | --- | --- |
| iii run 1 | 69.9% (1586.6) | 64.8% (1470.6) | 2.83 | 1.94 |
| iii run 2 | 59.8% (1349.6) | 56.4% (1272.7) | 3.03 | 1.96 |
| iii run 3 | 65.7% (1323.9) | 61.0% (1229.4) | 2.51 | 1.96 |
| i | 46.8% (704.4) | 32.3% (486.7) | 4.46 | 1.93 |
| iv | 22.3% (472.7) | 10.3% (218.6) | 5.80 | 2.08 |
| ii | 21.7% (149.0) | 11.8% (80.5) | 7.53 | 2.24 |

Powder X-ray diffraction was obtained using a Miniflex® 600 (Rigaku®, Woodlands, TX, USA) on the starting niclosamide material as well as the thin film frozen formulations. The diffraction pattern was scanned from 5° to 40° at a step size of 0.02°/min and continuous scanning speed of 2°/min with an accelerating voltage of 40 kV and 15 mA. See FIG. 15.

After these compositions were prepared, additional compositions that contained both the above hydrophilic excipients along with a hydrophobic excipients. In the preparation for manufacturing of these compositions, niclosamide and hydrophobic excipients (e.g. magnesium stearate, 1,2-dioctadecanoyl-sn-glycero-3-phosphocholine) were dissolved in TBA, comprising the organic phase. The hydrophilic excipients (e.g. mannitol, leucine, Captisol® (sulfobutylether-β-cyclodextrin), lactose monohydrate) were dissolved in water, which formed the aqueous phase. Then, the aqueous and organic phases were mixed as specified in Table 14.

Thereafter, the mixed solution was applied as drops onto a rotating cryogenically cooled drum at cooled to −120° C. The frozen solids were collected with liquid nitrogen and stored in a −80° C. freezer before lyophilization. The primary drying process was at −40° C. for 20 h, and then, the temperature was linearly increased to 25° C. over 20 h, followed by holding the temperature at 25° C. for 20 h. The pressure was maintained at 100 mTorr during the lyophilization process.

TABLE 14

Composition of the aqueous and organic phases for each DPI formulation.

| Code name | Composition | Organic phase composition (mg/mL) | | Aqueous phase composition (mg/mL) | Organic/Aqueous phase ratio |
|---|---|---|---|---|---|
| | | Niclosamide concentration | Other excipients | | |
| DPI 1 | 20% Niclosamide-64% Mannitol-16% DSPC | 1.563 mg/mL | DSPC 1.25 mg/mL | Mannitol 20 mg/mL | 80/20 |
| DPI 2 | 19% Niclosamide-75% Mannitol-6% DSPC | 1.875 mg/mL | DSPC 0.625 mg/mL | Mannitol 30 mg/mL | 80/20 |
| DPI 3 | 19% Niclosamide-81% Captisol ® | 0.5 mg/mL | | Captisol - 5 mg/mL | 70/30 |
| DPI 4 | 17.90% Niclosamide-76.72% Captisol ®-5.37% DSPC | 0.5 mg/mL | DSPC 0.15 mg/mL | Captisol - 5 mg/mL | 70/30 |
| DPI 5 | 23.71% Niclosamide-75.87% Mannitol-0.42% Mg St | 1.5625 mg/mL | Mg St. 0.0275 mg/mL | Mannitol 20 mg/mL | 80/20 |
| DPI 6 | 20% Niclosamide-79% Lactose-1% Mg St | 1.5 mg/mL | 0.0625 mg/mL | Lactose Monohydrate 19.75 mg/mL | 80/20 |
| DPI 7 | 22% Niclosamide-73% Mannitol-5% Leucine | 1.5 mg/mL | | Mannitol 20 mg/mL Leucine 1.3 mg/mL | 80/20 |
| DPI 8 | 50% Mannitol - 50% Niclosamide | 1.5 mg/mL | | Mannitol 5.0 mg/mL | 80/20 |

(Mg St. = magnesium stearate, DSPC = 1,2-dioctadecanoyl-sn-glycero-3-phosphocholine)

These compositions were then tested and show the aerosol performance listed in the Table below outlined above. See Table 15.

TABLE 15

Aerosol performance of screened formulations

| Formulation | Code name | Total Dose Per Shot [µg] | Calc Delivered Dose [µg] | Fine Particle Dose [µg] | Fine Particle Fraction [%, delivered dose] | Fine Particle Fraction (%, recovered dose) | MMAD [µm] | GSD |
|---|---|---|---|---|---|---|---|---|
| 20% Niclosamide-64% Mannitol-16% DSPC | DPI 1 | 1018.8 (84.5) | 841.0 (90.7) | 539.6 (171.2) | 63.2 (14.9) | 52.3 (13.2) | 2.12 (0.38) | 2.47 (0.12) |
| 18.75% Niclosamide-75% Mannitol-6.25% DSPC | DPI 2 | 1059.8 (85.3) | 913.5 (92.4) | 591.7 (53.1) | 64.9 (4.1) | 55.8 (2.3) | 2.11 (0.08) | 2.33 (0.19) |
| 18.92% Niclosamide-81.08% Captisol ® | DPI 3 | 859.9 (6.01) | 746.5 (40.0) | 276.7 (80.6) | 32.2 (9.3) | 27.4 (5.8) | 4.13 (0.59) | 2.40 (0.25) |

TABLE 15-continued

Aerosol performance of screened formulations

| Formulation | Code name | Total Dose Per Shot [µg] | Calc Delivered Dose [µg was quantified using HPLC-MS. In the case of lung tissue, the lungs were washed and perfused with PBS, removed, and immediately frozen. Prior to analysis, whole lung tissue was placed into BioStor™ Vials with screw caps (National Scientific Supply, Claremont, CA, USA) with 3.5 g of zirconia/silica beads (BioSpec Products, Bartlesville, OK, USA). The tissue was homogenized at 4,800 rpm for 20 seconds.

ii. Quantification of Niclosamide in Hamster's Plasma and Lung Tissue

The calibrators were prepared by spiking niclosamide standard solutions into blank plasma solutions with a range from 0.1 to 1000 ng/mL. 200 μL of a 100 ng/mL methanolic solution of the internal standard, $^{13}C6$ niclosamide (Niclosamide-(2-chloro-4-nitrophenyl-$^{13}C6$) hydrate, (Sigma-Aldrich®, Saint Louis, MO, USA) was added into 200 μL of plasma samples and calibrators. Then, they were vortexed and centrifuged for 15 min at 12,000 rpm. The supernatant was measured by LC/MS/MS analysis. In the case of lung tissue, the calibrators were prepared by spiking niclosamide standard solutions into blank lung tissue in the range from 0.5 to 10,000 g/mL. 1000 μL of internal standard, $^{13}C6$ niclosamide, at 100 ng/mL was added into the weighed lung samples and calibrators. Then, they were vortexed and centrifuged for 15 min at 12,000 rpm. The supernatant was measured by LC/MS/MS analysis. The analysis was performed using Agilent® G1367D autosampler, G4220A binary pump, G1316B column compartment, and a G6470A triple quadrupole mass spectrometer. Niclosamide was separated on an Agilent® poroshell column 2.1×50 mm, 2.7 μm column (Agilent Technologies®, Wilmington, DE, USA) using a gradient of 0 to 95% B in 5 min (A=water with 0.025% TFA and B=95% acetonitrile in water with 0.025% TFA) with a 1-minute hold at the final conditions at a flow rate of 0.35 mL/min. The post run column equilibration was 4 min. The column was held at 40° C. for the analysis. The injection volume for MS was 10 μL.

Remarkably, the inhaled powder achieved an MMAD of about 1 μm and was able to reach the last stage of the cascade impactor (FIGS. 18 & 19). Given treatment of patients potentially infected by SARS-CoV-2, delivering niclosamide into the deep lung region with the dry powder formulations is desirable, and this formulation warrants further development.

ii. Evaluation of Brittle Matrix Niclosamide in Reducing Viral Titers.

In order to evaluation brittle matrix niclosamide, Vero cells were seeded into 6-well plate and infect with SARS-CoV-2. Then, a 2 mg/mL suspension of the powder was prepared by weighing out 10 mg of the powder. To which, 5 mL of cell culture media was added inside a sterile environment. A dispersed suspension was generated using vortexing and sonication until all clumps of powder are broken up. The suspension should not be filtered. The suspension may be centrifuged to reduce foaming but was sonicated to redisperse particles prior to further dilutions. From this point forward, all work was carried out in a sterile environment. The NIC-TFF suspension was diluted 10× to generate 1 mL of a 100 μg/mL niclosamide suspension (stock A). Then, again the 100 μg/mL suspension 10× was diluted to generate 1 mL of a 10 μg/mL niclosamide suspension (stock B). The dilutions were prepared for cell treatments according to Table 17. Then, the cell culture media was replaced with the prepared suspensions according to FIG. 23C. The plate is prepared in triplicate. The viral viability was tested 24 hours after dosing. The results from the other treatment group are summarized in Table 18 below.

TABLE 17

Study design for in vitro evaluation of NIC-TFF powder

| Group | NIC conc (μg/mL) |
|---|---|
| NIC-TFF-2 | 2.0 |
| NIC-TFF-1 | 1.0 |
| NIC-TFF-0.5 | 0.5 |
| NIC-TFF-0.25 | 0.25 |
| NIC-TFF-0.125 | 0.125 |

TABLE 18

Results of 24 hour exposure with NIC-TFF powder formulation

| NIC conc (μg/mL) | Average reduction in SARS-CoV-2 viral titers versus untreated control |
|---|---|
| 2 | 15.0 ± 26.0 |
| 1 | 2.3 ± 4.0 |
| 0.5 | 90.2 ± 2.7 |
| 0.25 | 33.6 ± 26.6 |
| 0.125 | 0.0 ± 0.0 |

D. Nebulized Niclosamide Formulations

I. Sample 1

Suspensions of micronized niclosamide (NIC-M) was prepared at concentrations of 1.5 mg/mL, 3 mg/mL, and 6 mg/mL. All suspensions were prepared in 0.9% w/v sodium chloride (normal saline; NS) containing 0.2 mg/mL polysorbate 80. This concentration of polysorbate 80 was selected as it is the maximum concentration currently approved for inhaled products by the Food and Drug Administration (FDA).

The suspensions were prepared using the following protocol:
 a. Wet NIC-M powder with a sufficient volume of polysorbate 80, 10 mg/mL stock solution to achieve the final desired concentration of 0.2 mg/mL polysorbate 80.
 b. Add a volume of NS to that is equivalent to half the final desired volume of the suspensions. Mix well, using an ultrasonicator to assist with incorporation of powder into the dispersing media.
 c. Homogenize the suspension with a saw-tooth bladed rotor stator homogenizer at 30,000 RPM for 1 minute.
 d. Rinse the homogenizer blades with the remaining volume of NS to reach the final desired volume of the suspension. Homogenize again at 30,000 RPM for 1 minute.
 e. Centrifuge the suspensions at 118×g for 5 minutes to reduce foam
 f. Sonicate the suspensions to redisperse particles The particle size distribution of the suspensions is shown in FIG. 11.

Since the resulting particle size distribution of the suspensions was unsuitable for nebulization and lung deposition, these suspensions were not tested further using the nebulizer.

II. Sample 2

Suspensions of micronized niclosamide (NIC-M) was prepared at concentrations of 3 mg/mL and 5 mg/mL. All suspensions were prepared in 0.9% w/v sodium chloride (normal saline; NS) containing varying concentrations of bovine serum albumin (BSA). BSA was selected as an exemplary protein; in practice, a different therapeutic protein could be used that does not cause an immunological response.

The suspensions were prepared using the following protocol:

a. Combine NIC-M powder and BSA powder
b. Add a volume of NS to that is equivalent to 80% of the final desired volume of the suspensions. Mix well, using an ultrasonicator to assist with incorporation of powder into the dispersing media.
c. Homogenize the suspension with a saw-tooth bladed rotor stator homogenizer at 30,000 RPM for 1 minute.
d. Rinse the homogenizer blades with the remaining volume of NS to reach the final desired volume of the suspension. Homogenize again at 30,000 RPM for 1 minute.
e. Centrifuge the suspensions at 118×g for 5 minutes to reduce foam
f. Sonicate the suspensions to redisperse particles The particle size distribution of the suspensions is shown in FIG. 12.

The suspension containing 3 mg/mL NIC-M, 100 mg/mL BSA was selected for nebulization, as its particle size distribution was closest to that of the original powder.

Aerosolization of the NIC-M suspension was tested using two different nebulizers: the PARI® LC Sprint, a jet nebulizer, and the Aerogen® Solo, a vibrating mesh nebulizer. The devices were actuated in a Next Generation Impactor (NGI) that was previously chilled to 4° C., as specified by the United States Pharmacopeia. The flow rate was set to 15 mL/min and the devices were allowed to run for 2 minutes. Niclosamide deposited in the induction port and stages of the NGI was collected and quantified.

A quantifiable mass of drug could not be collected from the Aerogen® Solo test. The mass emitted and fine particle dose for the PARI® LC Sprint is shown in Table 19, while the stage deposition is shown in FIG. 13.

TABLE 19

Emitted Niclosamide Mass After Nebulization using PARI ® LC Sprint

|  | Per 2 minutes (total actuation time tested) | Per minute |
|---|---|---|
| Mass emitted (mg) | 0.32 | 0.16 |
| Fine particle dose ≤ 5 µm (mg) | 0.15 | 0.08 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. Pat. No. 8,968,786
U.S. Patent App. No. 2010/0221343
Ahmed et al., *Viruses*, 12:254, 2020.
Barbosa et al., *Eur. J. Pharm. Biopharm.*, 141:58-69, 2019.
Beinborn et al., *European journal of pharmaceutics and biopharmaceutics*, 81(3):600-8, 2012a.
Beinborn et al., *Int J Pharmaceut.*, 429(1-2):46-57, 2012b.
Bray et al., *CA: A Cancer Journal For Clinicians*, 68(6): 394-424, 2018.
Carvalho et al., *European journal of pharmaceutics and biopharmaceutics*, 88(1):136-47, 2014.
Chen et al., *Cell. Signal.*, 41:89-96, 2018.
Circu et al., *PLOS ONE*, 11:e0146931, 2016.
DiNunzio et al., *Mol Pharm.*, 5(6):968-80, 2008.
DiNunzio et al., *Drug Development and Industrial Pharmacy*, 36(9):1064-78, 2010d.
DiNunzio et al., *European Journal of Pharmaceutical Sciences*, 40(3):179-87, 2010c.
DiNunzio et al., *European Journal of Pharmaceutics and Biopharmaceutics*, 74(2):340-51, 2010a.
DiNunzio et al., *Journal of Pharmaceutical Sciences*, 99(3):1239-53, 2010b.
Dunay et al., *Antimicrobial agents and chemotherapy*; 48(12):4848-54, 2004.
Engstrom et al., *Pharm Res.*; 25(6):1334-46, 2008.
Fang et al., *Lancet Respir. Med.*, 2020.
Fonseca et al., *J. Biol. Chem.*, 287:17530-17545, 2012.
Friesen et al., *Molecular pharmaceutics*, 5(6):1003-19, 2008.
Gassen et al., *Nat. Commun.*, 10:1-16, 2019.
Gurwitz, D. *Drug Dev. Res.*, 2020.
Handbook of Pharmaceutical Salts: Properties, and Use (P. H. Stahl & C. G. Wermuth eds., Verlag Helvetica Chimica Acta, 2002).
Hoffmann et al., *Cell*, 2020.
Ippolito et al., *PloS One*, 11:e0159675, 2016.
Jeon et al., 2020.
Jurgeit et al., *PLoS Pathog.*, 8, 2012.
Kim and Ryan, *Current Treatment Options in Oncology*, 13(2):189-200, 2012.
Lang et al., *Mol Pharm.*, 11(1):186-96, 2014b.
Lang et al., *J Drug Deliv Sci Tec.*, 24(2):205-11, 2014a.
Li et al., *Cancer research*, 73(2):483-9, 2013.
Li et al., *Cancer letters*, 349(1):8-14, 2014.
Liu et al., *European journal of pharmaceutics and biopharmaceutics*, 96:132-42, 2015.
Liu et al., *Oncotarget*, 7(22):32210, 2016.
Liu et al., *Clinical Cancer Research.*, 2014.
Liu et al., *The Prostate*, 75(13):1341-53. 2015.
Luedeker et al., *Crystal Growth & Design*, 16(6):3087-3100, 2016.
Matsubara et al., *Clinical Genitourinary Cancer*, 16(2): 142-8, 2018.
Mook et al., *Bioorg. Med. Chem.*, 23:5829-5838, 2015.
Mostaghel et al., *Clinical cancer research*, 2011.
O'Donnell et al., *Drug Dev Ind Pharm.*, 39(2):205-17, 2013.
Overhoff et al., *Pharm Res.*, 25(1):167-75, 2008.
Overhoff et al., *European journal of pharmaceutics and biopharmaceutics*, 65(1):57-67, 2007b.
Overhoff et al., *Int J Pharmaceut.*, 336(1):122-32, 2007a.
Overhoff et al., *J Drug Del Sci Tech.*, 19(2):89-98, 2009.
Peeri et al., *Int. J. Epidemiol.*, 2020.
Phillips et al., *J Pharm Pharmacol.*, 64(11):1549-59, 2012.

Purvis et al., *Aaps Pharmscitech.*, 8(3):E58, 2007.
Rothan & Byrareddy, *J. Autoimmun.*, 102433, 2020.
Sanphui et al., *Cryst. Growth Des.*, 12(9):4588-4599, 2012.
Savjani et al., *Pharmaceutics*, 195727, 2012.
Schweizer et al., *PloS one*, 13(6):e0198389, 2018.
Sinswat et al., *European journal of pharmaceutics and biopharmaceutics*, 69(3):1057-66, 2008.
Takabe et al., *Pharmaceutics*, 10(2):60, 2018.
Tam et al., *Nat. Commun.*, 9:1-11. 2018.
Thakkar et al., *Hum Vaccin Immunother*, 13(4):936-46, 2017.
Tharmalingam et al., *Sci. Rep.*, 8:3701, 2018.
Tortoric et al., *Nat. Struct. Mol. Biol.*, 26:481-489, 2019.
Vincent et al., *Virol. J.*, 2:69, 2005.
Walls et al., *Cell*, 2020.
Wang et al., *Genes Dev.*, 32:1105-1140, 2018.
Wang et al., *Aaps Pharmscitech.*, 15(4):981-93, 2014.
Wang et al., *Cell Res.*, 30:269-271, 2020.
Watts et al., *Int J Pharmaceut.*, 384(1-2):46-52, 2010.
Watts, et al., 2013.
Wen et al., *J. Med. Chem.*, 50:4087-4095, 2007.
WHO Director-General's opening remarks at the Mission briefing on COVID-19-12 Mar. 2020. www.who.int/dg/speeches/detail/who-director-general-s-opening-remarks-at-the-mission-briefing-on-covid-19-12-march-2020.
Wu et al., *J. Antimicrob. Agents Chemother.*, 48, 2693-2696, 2004.
Xu et al., *ACS Infect. Dis.*, 2020.
Yan et al., *Science*, 2020.
Yang et al., 2010.
Yang et al., *Int J Pharmaceut*, 361(1-2):177-88, 2008.
Zhang et al., *PloS one;* 6(11):e27970, 2011.
Zhang et al., *European journal of pharmaceutics and biopharmaceutics*, 82(3):534-44, 2012.

What is claimed is:

1. A pharmaceutical composition comprising:
(A) an active agent, wherein the active agent is niclosamide, a pharmaceutically acceptable salt thereof, a hydrate, or a co-crystal thereof; and
(B) a pharmaceutically acceptable polymer, wherein the pharmaceutically acceptable polymer is a copolymer of polyvinyl pyrrolidone and polyvinyl acetate; and
(C) a surfactant, wherein the surfactant is tocopheryl polyethylene glycol succinate;
wherein the pharmaceutical composition is formulated for oral administration and the active agent is present in the amorphous form and is phase separated in the pharmaceutical composition.

2. The pharmaceutical composition of claim 1, wherein the composition has been formulated through hot melt extrusion.

3. The pharmaceutical composition of claim 1, wherein the hot melt extrusion is conducted at a temperature from about 100° C. to about 240° C.

4. The pharmaceutical composition of claim 1, wherein the pharmaceutical composition comprises from about 5% w/w to about 90% w/w of the active agent.

5. The pharmaceutical composition of claim 1, wherein the pharmaceutical composition comprises from about 40% w/w to about 95% w/w of the pharmaceutically acceptable polymer.

6. The pharmaceutical composition of claim 1, wherein the pharmaceutical composition comprises from about 50% w/w to about 70% w/w of the pharmaceutically acceptable polymer.

7. The pharmaceutical composition of claim 1, wherein the pharmaceutical composition further comprises an excipient.

8. The pharmaceutical composition of claim 7, wherein the excipient is a further surfactant or emulsifier.

9. The pharmaceutical composition of claim 8, wherein the excipient is a composition of two or more excipients.

10. The pharmaceutical composition of claim 9, wherein the excipient is two or more surfactants or emulsifiers.

11. The pharmaceutical composition of claim 7, wherein the pharmaceutical composition comprises from about 1% w/w to about 20% w/w of a further excipient.

12. The pharmaceutical composition of claim 7, wherein the excipient is a mixture of three excipients present in a ratio from about 1:0.1:0.1 to about 0.1:1:1.

13. A method of preparing a pharmaceutical composition of claim 1 comprising:
(A) obtaining a pharmaceutically acceptable polymer, wherein the pharmaceutically acceptable polymer is a copolymer of polyvinyl pyrrolidone and polyvinyl acetate; a surfactant, wherein the surfactant is tocopheryl polyethylene glycol succinate; and an active agent, wherein the active agent is niclosamide, a pharmaceutically acceptable salt thereof, or a co-crystal thereof; and
(B) subjecting the pharmaceutically acceptable polymer, the surfactant, and the active agent to a hot melt extruder to obtain a pharmaceutical composition.

14. A method of reducing lung inflammation in a patient in need thereof comprising administering a pharmaceutical composition of claim 1 to the patient in a therapeutically effective amount.

* * * * *